(12) United States Patent
Wilk

(10) Patent No.: US 7,595,338 B2
(45) Date of Patent: Sep. 29, 2009

(54) PROCESS FOR PREPARING 3,3-DISUBSTITUTED OXINDOLES AND THIO-OXINDOLES

(75) Inventor: Bogdan Kazimierz Wilk, New City, NY (US)

(73) Assignee: Wyeth, Madison, NJ (US)

( * ) Notice: Subject to any disclaimer, the term of this patent is extended or adjusted under 35 U.S.C. 154(b) by 440 days.

(21) Appl. No.: 11/413,159

(22) Filed: Apr. 27, 2006

(65) Prior Publication Data

US 2006/0247441 A1    Nov. 2, 2006

Related U.S. Application Data

(60) Provisional application No. 60/676,381, filed on Apr. 29, 2005.

(51) Int. Cl.
*A61K 31/404* (2006.01)
*C07D 209/34* (2006.01)

(52) U.S. Cl. .................................. 514/418; 548/486
(58) Field of Classification Search ............. 548/408, 548/465, 411, 486
See application file for complete search history.

(56) References Cited

U.S. PATENT DOCUMENTS

| | | | |
|---|---|---|---|
| 3,732,278 | A | 5/1973 | Norris |
| 4,555,370 | A | 11/1985 | Klauke et al. |
| 4,783,547 | A | 11/1988 | Hartmann et al. |
| 4,866,185 | A | 9/1989 | Hartmann et al. |
| 4,886,833 | A | 12/1989 | Gayer et al. |
| 4,939,172 | A | 7/1990 | Cadiergue et al. |
| 4,965,394 | A | 10/1990 | Hartmann et al. |
| 5,231,109 | A | 7/1993 | Gayer et al. |
| 5,288,732 | A | 2/1994 | Gayer et al. |
| 5,545,769 | A | 8/1996 | Baker et al. |
| 5,670,679 | A | 9/1997 | Baker et al. |
| 5,760,282 | A | 6/1998 | Baker et al. |
| 5,811,587 | A | 9/1998 | Moreau et al. |
| 5,847,005 | A | 12/1998 | Kasahara et al. |
| 5,942,538 | A | 8/1999 | Kasahara et al. |
| 6,005,118 | A | 12/1999 | Caron |
| 6,040,487 | A | 3/2000 | Baker et al. |
| 6,184,418 | B1 | 2/2001 | Dubac et al. |
| 6,291,730 | B1 | 9/2001 | Baker et al. |
| 6,303,782 | B1 | 10/2001 | Caron |
| 6,482,983 | B1 | 11/2002 | Lebedev et al. |
| 6,777,409 | B2 | 8/2004 | Jaroch et al. |
| 2003/0224284 | A1 | 12/2003 | Tao |
| 2004/0077669 | A1 | 4/2004 | Mizuno et al. |
| 2005/0222148 | A1* | 10/2005 | Kim et al. ............ 514/232.5 |

FOREIGN PATENT DOCUMENTS

| | | |
|---|---|---|
| DE | 3909213 | 10/1990 |
| DE | 19529089 | 2/1997 |
| EP | 10879 | 5/1980 |
| EP | 041021 | 12/1981 |
| EP | 313076 | 4/1989 |
| EP | 1046635 | 10/2000 |
| FR | 2745285 | 8/1997 |
| FR | 2745287 | 8/1997 |
| WO | WO 93/11118 | 6/1993 |
| WO | WO 94/08982 | 4/1994 |
| WO | WO 98/15180 | 4/1998 |
| WO | WO 00/08000 | 2/2000 |
| WO | WO 02/10143 | 2/2002 |
| WO | WO 03/006015 | 1/2003 |
| WO | WO 03/087067 | 10/2003 |
| WO | WO-2005/097733 | 10/2005 |

OTHER PUBLICATIONS

Caron et al., "Preparation of Tertiary Benzylic Nitriles from Aryl Fluorides", J. Am. Chem. Soc., 122:712-713 (2000).
Caron et al., "Nucleophilic Aromatic Substitution of Aryl Fluorides by Secondary Nitriles: Preparation of 2-(2-methoxyphenyl)-2-methylpropionitrile", Org. Syn., Coll. 10:505 (2004).
Fleming et al., "Two New Stereochemically Complementary Oxindole Syntheses" Tet. Lett 23(19):2053-2056 (1982).
Fleming et al., "Two New Oxindole Syntheses", Chem. Soc. Perkin Trans. I, 349 (1986).
Lebedev et al., "Lower Primary Alkanols and Their Esters in a Ritter-Type Reaction with Nitriles. An Efficient Method for Obtaining N-Primary-Alkyl Amides", Tet. Lett., 43:1397-1399 (2002).
Katsuta, Abstract of Japanese Patent No. JP-58-116404-A (Jul. 11, 1983).
Ito et al., Abstract of Japanese Patent No. JP-08-143579 (Jun. 4, 1996).
Kasahara et al., Abstract of Japanese Patent No. JP-09-235262-A2 (Sep. 9, 1997).
Kasahara et al., Abstract of Japanese Patent No. JP-10-067730 (Mar. 10, 1998).
Shigeru et al., Abstract of Japanese Patent No. JP-03-145447-A (Jun. 20, 1991).
Takahashi et al. Abstract of Japanese Patent No. JP-05-331004 (Dec. 14, 1993).
Ishizaki et al. Abstract of Japanese Patent No. JP-05-339224-A (Dec. 21, 1993).
Luft et al., "Polyethylene Production by High Pressure Process", Abstract of European Patent No. EP 0 313 076 (Oct. 21, 1988).
Baudry et al., Abstract of French Patent No. FR2745285 (Aug. 29, 1997).

(Continued)

*Primary Examiner*—Kamal A Saeed
*Assistant Examiner*—Kristin Bianchi
(74) *Attorney, Agent, or Firm*—Paul Carango, Esq.; Howson & Howson LLP

(57) ABSTRACT

Methods for preparing oxindole and thio-oxindole compounds are provided, which compounds are useful as precursors to useful pharmaceutical compounds. Specifically provided are methods for preparing 5-pyrrole-3,3-oxindole compounds and 5-(7-fluoro-3,3-dimethyl-2-oxo-2,3-dihydro-1H-indol-5-yl)-1-methyl-1H-pyrrole-2-carbonitrile.
Also provided are methods for preparing iminobenzo[b]thiophene and benzo[b]thiophenone compounds.

13 Claims, No Drawings

OTHER PUBLICATIONS

Baudry et al., "Catalytic Composition Based on Rare Earth Deposited on Clay, Silica, and/or Alumina Support—Useful in the Acylation of (de)activated Aromatic Compounds to Form Aromatic Ketone(s)", Abstract of French Patent No. FR 2745287 (Aug. 29, 1997).

Dutzmann et al., "New Phenyl-(mercaptotriazolyl)-propionitrile Derivatives", Abstract of German Patent No. 195299089 (Aug. 8, 1995).

Fischer et al., "New Halobenzene Derivatives", Abstract of German Patent No. 3909213 (Mar. 21, 1989).

Cloudsdale et al., "Herbicidal Sufonylamides", in Synthesis and Chemistry of Agrochemicals IV, ACS Symposium Series, Baker et al., Eds., American Chemical Society, Washington, DC, 584: 37-45 (1995).

Plevey et al., "Synthesis of 3-(4-aminotetrafluyorophenyl)-3-ethylpiperidine-2,6-dione: A Fluorinated Derivatives of Aminoglutethimide", J. Chem. Soc., Perkin Trans. 1: Org. and Bioorg. Chem. 10:2129-2136 (1987).

Wheland et al., "Synthesis of Substituted 7,7,8,8-Tetracyanoquiinodimethanes", J. Org. Chem., 40(21):3103-3109 (1975).

Martel et al., "2,2-Dimethyl 3-alkoxycarbonyl-vinyl-cyclopropane Acid Ester", English Abstract of European Patent No. 41021 (Dec. 2, 1981).

Kawamura et al., "Studies on the Heterocyclic Chemistry. Part 26. The Ring Transformation of 3-Acylthio-4-aryl-3-isothiazoline-5-thiones to Benzo[d]- and Naphto[3,1-]-thiophenes with an Acylimino-Group at C-2 Via the 2-Arylethanethioamide Derivatives" J. Chem. Soc. Perkin Trans. 1, 1982:2867-2870 (1982).

* cited by examiner

PROCESS FOR PREPARING 3,3-DISUBSTITUTED OXINDOLES AND THIO-OXINDOLES

CROSS-REFERENCE TO RELATED APPLICATIONS

This application claims the benefit of the priority of U.S. Provisional Patent Application No. 60/676,381, filed Apr. 29, 2005.

BACKGROUND OF THE INVENTION

Methods for preparing oxindole and thio-oxindole compounds, particularly 5-pyrrole-3,3-oxindoles, which compounds are useful as precursors to various pharmaceutical compounds are provided.

The synthetic routes to many useful compounds, including pharmaceutical drugs, typically entail a large number steps. However, the presence of numerous steps in the synthetic route to the desired product tends to result in lower yields of the product even before purification.

Many useful compounds in the art have an oxindole backbone and particularly a 3,3-disubstituted oxindole backbone. Of particular interest is 5-(7-fluoro-3,3-dimethyl-2-oxo-2,3-dihydro-1H-indol-5-yl)-1-methyl-1H-pyrrole-2-carbonitrile, which contains a 3,3-disubstituted oxindole backbone. In fact, the current route to 5-(7-fluoro-3,3-dimethyl-2-oxo-2,3-dihydro-1H-indol-5-yl)-1-methyl-1H-pyrrole-2-carbonitrile involves at least 6 steps to give an overall yield of 6%.

What is needed in the art are alternate methods for preparing 3,3-disubstituted oxindole compounds and the intermediates utilized in preparation thereof.

SUMMARY OF THE INVENTION

In one aspect, methods for preparing oxindole compounds and, desirably, 3,3-disubstituted oxindole compounds are provided.

In another aspect, methods for preparing 5-pyrrole-3,3-oxindole compounds are provided.

In a further aspect, methods for preparing 5-(7-fluoro-3,3-dimethyl-2-oxo-2,3-dihydro-1H-indol-5-yl)-1-methyl-1H-pyrrole-2-carbonitrile are provided.

In yet another aspect, methods for preparing thio-oxindole compounds and, desirably, 3,3-disubstituted thio-oxindole compounds are provided.

In a further aspect, methods for preparing iminobenzo[b]thiophene compounds are provided.

In still another aspect, methods for preparing benzo[b]thiophenone compounds are provided.

In yet a further aspect, methods for preparing compounds of the structure are provided:

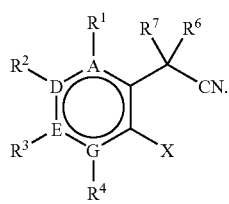

In another aspect, methods for selectively preparing a compound of the structure are provided:

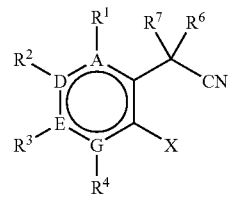

In still a further aspect, 2-(5-bromo-2-fluorophenyl)-2-methylpropionitrile; 2-(3-chloropyridin-2-yl)-2-methylpropionitrile; 2-(3-chloroquinoxalin-2-yl)-2-methylpropionitrile; 2-(2-fluorophenyl)-2-methylpropionitrile; 2-(2,3-difluorophenyl)-2-methylpropionitrile; 2-(2,6-difluorophenyl)-2-methylpropionitrile; 2-(2,3-difluorophenyl)isobutyramide; 2-(2,6-difluorophenyl)isobutyramide; 2-(2-fluorophenyl)isobutyramide; 2-(3-chloropyridin-2-yl)isobutyramide; 1-(2,6-difluorophenyl)cyclopropanecarboxylic acid amide; or a pharmaceutically acceptable salt thereof are provided.

Other aspects and advantages of the invention will be readily apparent from the following detailed description of the invention.

DETAILED DESCRIPTION OF THE INVENTION

A novel route to oxindole compounds and particularly 3,3-oxindole compounds is provided. Advantageously, a shorter route to oxindole compounds is also provided using 3 steps. The process includes converting a fluoroarene to a secondary nitrile substituted arene, converting the nitrile substituent to an amide, and cyclizing the amide to the oxindole compound.

Suitably, an oxindole prepared in the present method has the following structure:

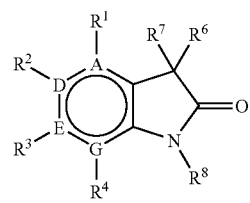

wherein, $R^1$, $R^2$, $R^3$, and $R^4$ are, independently, selected from among H, halogen, CN, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heteroaryl, substituted heteroaryl, $N_2^+$, $OSO_2CF_3$, $CF_3$, $NO_2$, $SR^5$, $OR^5$, $N(R^5)_2$, $COOR^5$, $CON(R^5)_2$, and $SO_2N(R^5)_2$; or $R^1$ and $R^2$; $R^2$ and $R^3$; $R^3$ and $R^4$; $R^1$, $R^2$, and $R^3$; or $R^2$, $R^3$, and $R^4$ are fused to form (i) a 3 to 15 membered saturated or unsaturated carbon-containing ring; or (ii) a 3 to 15 membered heterocyclic ring containing in its backbone from 1 to 3 heteroatoms selected from among O, S, and $NR^{11}$; $R^5$ is selected from among $C_1$ to $C_6$ alkyl and $C_1$ to $C_6$ substituted alkyl; $R^6$ and $R^7$ are, independently, selected from among $C_1$ to $C_6$ alkyl, substituted $C_1$ to $C_6$ alkyl, $C_3$ to $C_{14}$ cycloalkyl, substituted $C_3$ to $C_{14}$ cycloalkyl, aryl, substituted aryl, heteroaryl, substituted heteroaryl, $C_2$ to $C_6$ alkenyl, substituted $C_2$ to $C_6$ alkenyl, $C_2$ to $C_6$ alkynyl, substituted $C_2$ to $C_6$ alkynyl, $N(R^5)_2$, $SR^5$, and $OR^5$; or $R^6$ and $R^7$ are fused to form (iii) a 3 to 8 membered saturated or unsaturated carbon-containing ring; or (iv) a 3 to 8 membered heterocyclic ring containing in its backbone from 1 to 3 heteroatoms selected from among O, S, and $NR^{11}$; $R^8$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $CF_3$, aryl, substituted aryl, heteroaryl, and substituted heteroaryl; or $R^8$ is fused with $R^4$ to form (v) a 5 to 8 membered saturated or unsaturated carbon-containing ring; or (vi) a 5 to 8 membered heterocyclic ring containing in its backbone 1 to 3 heteroatoms selected from among O, S, and $NR^{11}$; wherein any of (i)-(vi) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$; $R^{11}$ is absent, H, $C_1$ to $C_6$ alkyl, substituted $C_1$ to $C_6$ alkyl, aryl, or substituted aryl; A, D, E, and G are, independently, selected from among C and N, wherein if any one of A, D, E, or G are N, the corresponding $R^1$-$R^4$ is optionally absent; or a pharmaceutically acceptable salt thereof. In one example, G is N. In another example, E and G are N. In a further example, D and G are N. In yet another example, A and G are N. In still a further example, $R^8$ is H. In yet another example, $R^8$ is cyclohexane. In a further example, $R^6$ and $R^7$ are fused to form an adamantane ring.

In one embodiment, oxindoles of the following structure are prepared, where $R^1$-$R^4$ and $R^6$-$R^8$ are defined above:

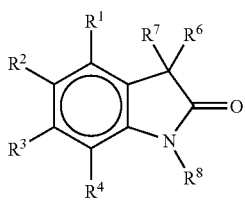

In another embodiment, the following oxindoles are prepared:

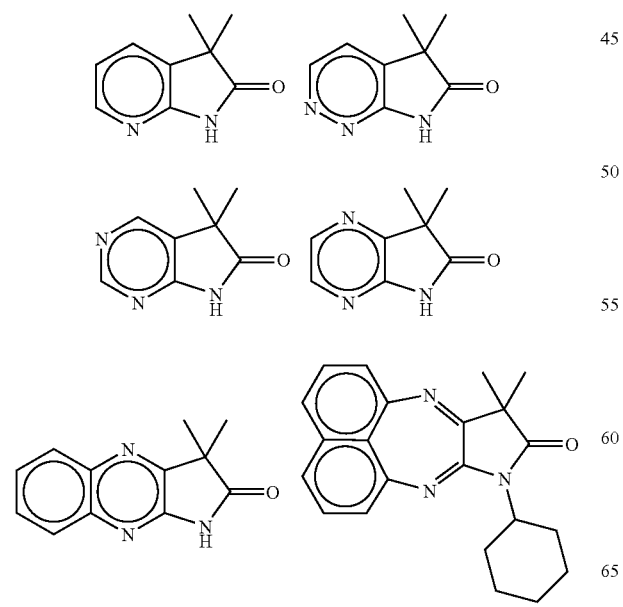

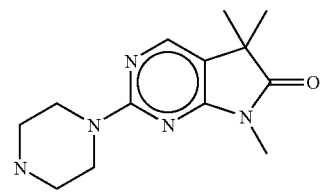

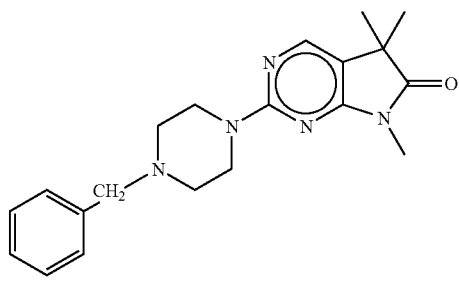

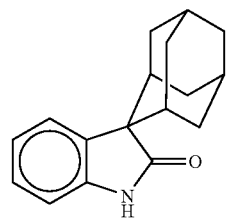

In a further embodiment, 5-(7-fluoro-3,3-dimethyl-2-oxo-2,3-dihydro-1H-indol-5-yl)-1-methyl-1H-pyrrole-2-carbonitrile is prepared.

In yet another embodiment, the following oxindoles are prepared:

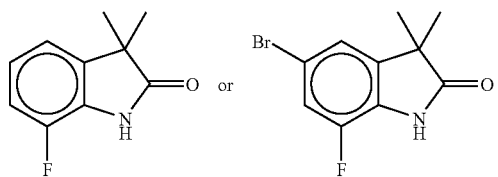

In still a further embodiment, the following oxindole compounds, which are covered by the compounds of US Patent Application Publication No. US 2005-0222148-A1 hereby incorporated by reference, are prepared.

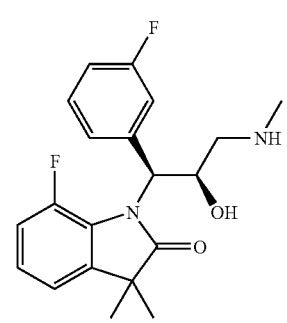

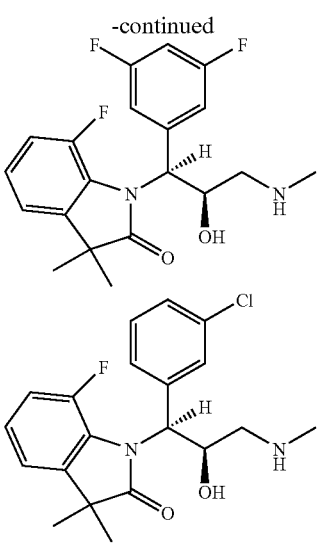

In yet another embodiment, the following oxindole compound, which is described in US Patent Application Publication No. US 2006-0030717-A1 hereby incorporated by reference, is prepared.

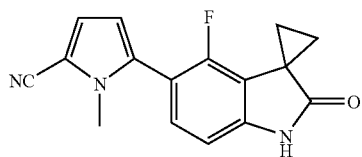

This oxindole compound is prepared using the following intermediates.

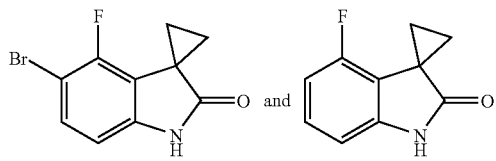

The term "alkyl" is used herein to refer to both straight- and branched-chain saturated aliphatic hydrocarbon groups having 1 to about 10 carbon atoms, desirably 1 to about 8 carbon atoms, and more desirably 1 to about 6 carbon atoms. The term "alkenyl" is used herein to refer to both straight- and branched-chain alkyl groups having one or more carbon-carbon double bonds and containing about 2 to about 10 carbon atoms. Desirably, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to about 8 carbon atoms. Desirably, the term alkynyl refers to an alkyl group having 1 or 2 carbon-carbon triple bonds and having 2 to about 6 carbon atoms.

The term "cycloalkyl" is used herein to refer to an alkyl group as previously described that is cyclic in structure and has 3 to about 10 carbon atoms, and desirably about 5 to about 8 carbon atoms.

The terms "substituted alkyl", "substituted alkenyl", "substituted alkynyl", and "substituted cycloalkyl" refer to alkyl, alkenyl, alkynyl, and cycloalkyl groups, respectively, having one or more substituents including, without limitation, halogen, CN, OH, $NO_2$, amino, aryl, heterocyclic, alkoxy, aryloxy, alkylcarbonyl, alkylcarboxy, and arylthio which groups can be optionally substituted. These substituents can be attached to any carbon of an alkyl, alkenyl, or alkynyl group provided that the attachment constitutes a stable chemical moiety.

The term "aryl" as used herein refers to an aromatic system which can include a single ring or multiple rings fused or linked together where at least one part of the fused or linked rings forms the conjugated aromatic system. Desirably, the aromatic system contains 6 to 14 carbon atoms. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group, desirably a $C_6$-$C_{14}$ aryl group, which is substituted with one or more substituents including halogen, CN, OH, $NO_2$, amino, alkyl, cycloalkyl, alkenyl, alkynyl, alkoxy, aryloxy, hydroxyalkyl, alkylcarbonyl, alkylcarboxy, aminoalkyl, and arylthio, which groups can be optionally substituted. Desirably, a substituted aryl group is substituted with 1 to about 4 substituents.

The term "heteroaryl" as used herein refers to a stable 5- to 14-membered monocyclic or multicyclic aromatic heterocyclic ring system. The heteroaryl ring has carbon atoms and one or more heteroatoms including nitrogen, oxygen, and sulfur atoms. Desirably, the heteroaryl ring has 1 to about 4 heteroatoms in the backbone of the ring. When the heteroaryl ring contains nitrogen or sulfur atoms in the backbone of the ring, the nitrogen or sulfur atoms can be oxidized.

The term "heterocyclic" refers to optionally saturated or partially saturated heterocyclic rings having 3 to 15 ring atoms, desirably 3 to 8 ring atoms, and desirably containing from 1 to 3 heteroatoms selected from among O, S and N. When the heterocyclic ring contains nitrogen or sulfur atoms in the backbone of the ring, the nitrogen or sulfur atoms can be oxidized. The term "heterocyclic" also refers to multicyclic rings in which a heterocyclic ring is fused to an aryl ring. The heterocyclic ring can be attached to the aryl ring through a heteroatom or carbon atom provided the resultant heterocyclic ring structure is chemically stable.

A variety of heterocyclic or heteroaryl groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, napthylridinyl, benzothienyl, pyridopyridinyl, benzoxazinyl, xanthenyl, acridinyl, and purinyl rings.

The term "substituted heterocyclic" or "substituted heteroaryl" as used herein refers to a heterocyclic group having one or more substituents including halogen, CN, OH, $NO_2$, amino, alkyl, cycloalkyl, alkenyl, alkynyl, alkoxy, aryloxy, hydoxyalkyl, alkylcarbonyl, alkylcarboxy, aminoalkyl, and arylthio, which groups can be optionally substituted. Desirably, a substituted heterocyclic group is substituted with 1 to about 4 substituents.

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "hydroxyalkyl" as used herein refers to the alkylOH group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different.

The term "thioalkoxy" or "thioalkyl" as used herein refers to the S(alkyl) group, where the point of attachment is through the sulfur-atom and the alkyl group is optionally substituted.

The term "halogen" as used herein refers to Cl, Br, F, or I groups.

The oxindoles discussed herein also encompass tautomeric forms and salts derived from pharmaceutically or physiologically acceptable acids, bases, alkali metals and alkaline earth metals. Also included are oxindole derivatives, including, but not limited to, esters, carbamates, sulfates, ethers, oximes, carbonates, and the like.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali metal salts and alkaline earth metal salts can include, without limitation, sodium, potassium, calcium and magnesium salts in the form of esters, and carbamates.

These salts can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The oxindoles discussed herein also encompass "metabolites" which are unique products formed by processing of the oxindole by the cell or patient. Desirably, metabolites are formed in vivo.

Methods of preparing oxindole compounds, desirably 3,3-disubstituted-oxindoles, are thereby provided. Oxindoles IV are prepared by substituting fluoroarene I with a secondary nitrile to form nitrile II, converting nitrile II to amide III, and cyclizing amide III to form oxindole IV. Alternatively, nitrile II can first be converted to acid V and thereby to amide III. See, Scheme 1, where $R^1$-$R^4$, $R^6$, $R^7$, and $R^8$ are defined above and X is defined below.

Scheme 1

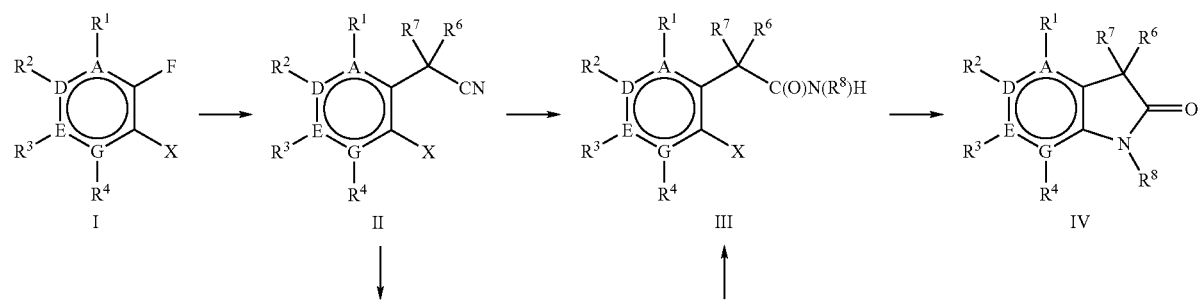

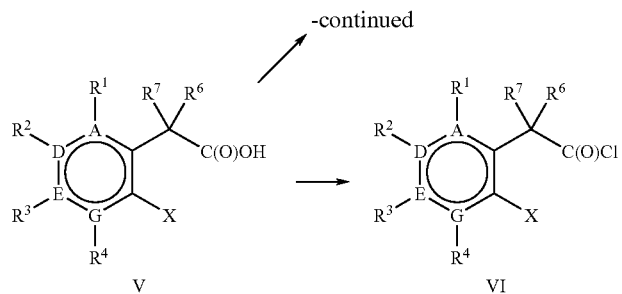

The method utilizes fluoroarene I as the starting material. Desirably, the fluoroarene has the following structure and contains a halogen in the ortho position (X).

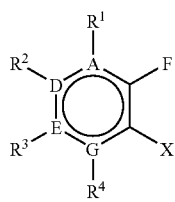

wherein, $R^1$-$R^4$, A, D, E, and G are defined above. More desirably, X is fluorine.

In one embodiment, the fluoroarene is of the following structure, wherein $R^1$-$R^4$ and X are defined above:

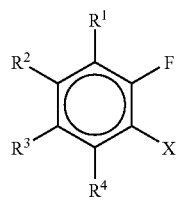

In another embodiment, the fluoroarene is of the following structure:

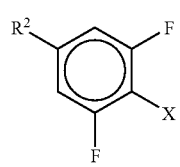

wherein, X is F, Cl, or Br; and $R^2$ is Br, Cl, I, or H.

In a further embodiment, the fluoroarene is selected from among:

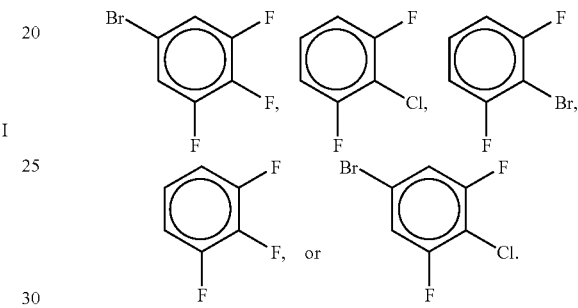

The fluoroarene is subsequently reacted with a secondary nitrile to undergo a nucleophilic aromatic substitution. See, for example the reagents utilized in the substitution reaction described in U.S. Pat. No. 6,303,782; JACS 2000, 122, 712; Org. Synth. 2002, 79, 209; and European Patent No. 1,046,635, which are hereby incorporated by reference. Typically, the secondary nitrile is $R^6R^7$CHCN, wherein $R^6$ and $R^7$ are defined above. This reaction is typically performed in the presence of a base including silyl reagents such as sodium hexamethyldisilazide (NaHMDS), potassium hexamethyldisilazide (KHMDS), lithium hexamethyldisilazide (LiHMDS); lithium diisopropylamide (LDA); Grignard reagents such as isopropyl magnesium halide including isopropyl magnesium chloride ($^i$PrMgCl), methyl magnesium bromide (MeMgBr), vinyl magnesium bromide (vinylMgBr), o-tolyl magnesium bromide, and dibutyl magnesium chloride; sodium hydride (NaH); 1,1,3,3-tetramethylguanidine (TMG); methyl lithium (MeLi); hexyl lithium (HexLi); potassium t-butoxide (t-BuOK); potassium t-pentoxide (t-PentOK), among others. Desirably, the base is a silyl reagent, a Grignard reagent, or LDA. More desirably, the base is sodium hexamethyldisilazide, potassium hexamethyldisilazide, lithium hexamethyldisilazide, lithium diisopropylamide, isopropyl magnesium chloride, methyl magnesium bromide, o-tolyl magnesium bromide, or dibutyl magnesium chloride. More desirably, the base is a Grignard reagent including isopropyl magnesium chloride, methyl magnesium bromide, o-tolyl magnesium bromide, or dibutyl magnesium chloride.

The process described herein also permits selective conversion of fluoroarene I to nitrile II by reducing the production of undesired by-products. By-products include isomers of nitrile II formed by reaction of the secondary nitrile with substituents other than the fluorine atom at the 1-position of fluoroarene I. In one embodiment, the secondary nitrile reacts with one or more of the X or $R^1$-$R^4$ substituents of fluoroarene I to form by-product(s). By doing so, the process thereby provides higher yields of the desired nitrile II product.

The inventors have found that when a Grignard reagent is utilized as the base for conversion of fluoroarene I to nitrile II, fewer by-products were formed. Suitable Grignard reagents include those described above. Further, use of a lower temperature promoted conversion of fluoroarene I to nitrile II. The term "lower temperatures" as used herein for this conversion includes temperatures of about −40 to 0° C. Most desirably, the temperature is about −25° C. The inventors therefore found that the combination of the Grignard reagent and lower temperature afforded nitrile II in good yields with the least amount of by-products, particularly when X is a fluorine atom.

The inventors have also found that preparation of nitrile II from fluoroarene I is desirable over the preparation of nitrile II via alkylation of the α-carbon of the corresponding benzylnitrile compound as described in I. Fleming, et al, J. Chem. Soc., Perkin Trans. I, 1986, 349, which is hereby incorporated by reference. Specifically, alkylation of the benzylnitrile as described by Fleming is difficult to control and results in a mixture of by-products including mono- and di-alkylated nitriles, as well as unreacted benzylnitrile starting material. Further, separation of nitrile II from any by-product and/or unreacted benzylnitrile not only requires a separate step, but the procedure for separation is difficult, thereby resulting in lower yields of nitrile II. However, the use of fluoroarene I to prepare nitrile II, as described in the present application, eliminates the generation of the alkylated by-products described by Fleming.

A nitrile of the following structure is thereby prepared.

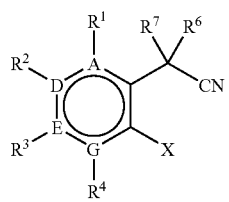

II wherein, $R^1$-$R^4$, A, D, E, G, X, $R^6$, and $R^7$ are defined above.

In one embodiment, a nitrile of the following structure is prepared:

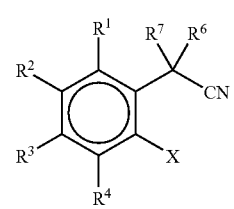

In another embodiment, a nitrile of the following structure is prepared.

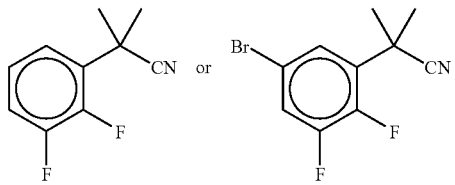

In a further embodiment, 2-(5-bromo-2-fluorophenyl)-2-methylpropionitrile; 2-(3-chloropyridin-2-yl)-2-methylpropionitrile; 2-(3-chloroquinoxalin-2-yl)-2-methylpropionitrile; 2-(2-fluorophenyl)-2-methylpropionitrile; 2-(2,3-difluorophenyl)-2-methylpropionitrile; and 2-(2,6-difluorophenyl)-2-methylpropionitrile are prepared.

The nitrile group of nitrile compound II is then converted to amide III of the following structure using techniques known to those of skill in the art including, without limitation, those transformations described in Larock, *Comprehensive Organic Transformations*, John Wiley & Sons, New York, N.Y., (1999); U.S. Pat. No. 6,482,983; Fleming, 1986, cited above; and Lebedev et al., Tet. Lett. 43:1397-1399 (2002), which are hereby incorporated by reference.

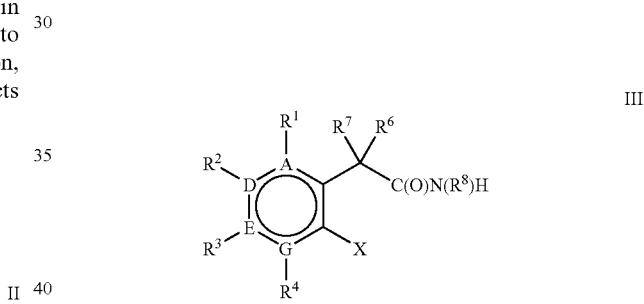

III wherein, $R^1$-$R^4$, $R^6$, $R^7$, and X are defined above and $R^8$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $CF_3$, aryl, substituted aryl, heteroaryl, and substituted heteroaryl.

In one embodiment, nitrile II is converted to amide III using basic or acidic hydrolysis. In one example, nitrile II is converted to amide III using Ritter or Ritter-type reactions as described in U.S. Pat. No. 6,482,983; and Lebedev cited above. In another example, amide III is prepared by reacting nitrile II with an alcohol, sulfonate, phosphate, ester, or boronic ester. In a further example, amide III is prepared by reacting nitrile II with $(R^8O)_nZ$, where $R^8$ is selected from among H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $CF_3$, aryl, substituted aryl, heteroaryl, and substituted heteroaryl, n is 0 to 3, and Z is H when n is 1, $SO_2$ when n is 2, P═O when n is 3, C═O when n is 2, B when n is 3, $SO_2$alkyl when n is 1, $(C═O)_2$ when n is 2, and acetyl when n is 1, under acidic or basic conditions. One of skill in the art would readily be able to select suitable reagents for either acidic or basic hydrolysis and include those described in Larock cited above and incorporated by reference. Basic hydrolysis to amide III can be performed with hydrogen peroxide and a base readily selected by one of skill in the art. Acidic hydrolysis to amide II can be performed using a strong acid, such as sulfuric acid, methanesulfonic acid, or hydrochloric acid.

In one embodiment, amides of the following structure are prepared.

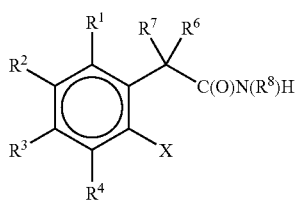

In another embodiment, amides of the following structures are prepared.

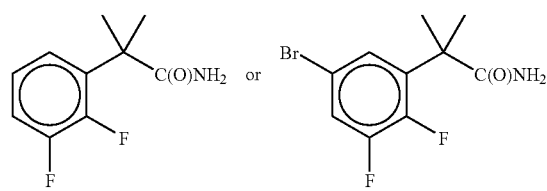

In a further embodiment, 2-(2,3-difluorophenyl)isobutyramide; 2-(2,6-difluorophenyl)isobutyramide; 2-(2-fluorophenyl)isobutyramide; 2-(3-chloropyridin-2-yl)isobutyramide; 1-(2,6-difluorophenyl)cyclopropanecarboxylic acid amide are prepared.

Amide III is alternatively prepared by first converting nitrile II to an acid V of the following structure, where $R^1$-$R^4$, $R^6$, $R^7$, X, A, D, E, and G are defined above, which is subsequently converted to the amide III noted above.

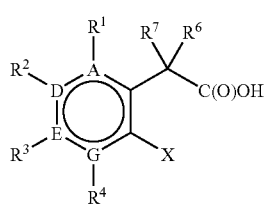

Conversion of nitrile II to acid V to amide III can be performed using the transformations set forth in Larock cited above or U.S. Pat. No. 6,482,983, which are hereby incorporated by reference. In one example, nitrile II is hydrolyzed to acid V, which is reacted with an amine, desirably at elevated temperatures in the presence of p-toluenesulfonic acid, to prepare amide III. In another example, nitrile II is hydrolyzed to acid V, acid V is converted to acid chloride VI, and acid VI is converted to amide III using the transformations set forth in Larock; Fleming, 1986; or U.S. Pat. No. 6,482,983 cited above.

Amide III is then treated with a strong base that is capable of deprotonating the hydrogen-atom of the amide functional group. Deprotonation of the amide results in the formation of the amide anion, which reacts with the halo group in the ortho position (X) to cyclize to the oxindole IV. One of skill in the art could readily select a suitable strong base to cyclize the amide and includes those reagents set forth in Fleming, Tetrahedron Lett., 1982, 23, 2053 and J. Chem. Soc., Perkin Trans. I, 1986, 349, which are hereby incorporated by reference, among others. Desirably, the strong base is lithium hydride, lithium diisopropylamide, alkyl lithium reagents, aryl lithium reagents, lithium hexamethyldisilazide, sodium hexamethyldisilazide, and potassium hexamethyldisilazide, among others.

Also provided are methods for preparing 5-pyrrole-3,3-oxindole compounds of the structure:

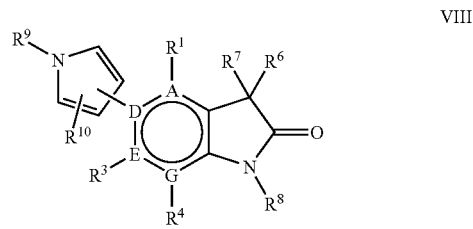

wherein, $R^1$, $R^3$, and $R^4$ are, independently, selected from among H, chlorine, CN, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heteroaryl, substituted heteroaryl, $OSO_2CF_3$, $CF_3$, $NO_2$, $SR^5$, $OR^5$, $N(R^5)_2$, $COOR^5$, $CON(R^5)_2$, and $SO_2N(R^5)_2$; or $R^1$ and $R^2$; $R^2$ and $R^3$; $R^3$ and $R^4$; $R^1$, $R^2$, and $R^3$; or $R^2$, $R^3$, and $R^4$ are fused to form (i) a 3 to 15 membered saturated or unsaturated carbon-containing ring; or (ii) a 3 to 15 membered heterocyclic ring containing in its backbone from 1 to 3 heteroatoms selected from among O, S, and $NR^{11}$; $R^5$ is selected from among $C_1$ to $C_6$ alkyl and $C_1$ to $C_6$ substituted alkyl; $R^6$, $R^7$, $R^8$, A, D, E, and G are defined above; $R^9$ is $C_1$ to $C_6$ alkyl, substituted $C_1$ to $C_6$ alkyl, aryl, substituted aryl, heteroaryl, substituted heteroaryl, or $COR^A$; $R^A$ is H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, or substituted $C_1$ to $C_6$ aminoalkyl; and $R^{10}$ is H, OH, $NH_2$, CN, halogen, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_1$ to $C_6$ alkoxy, substituted $C_1$ to $C_6$ alkoxy, $C_1$ to $C_6$ aminoalkyl, substituted $C_1$ to $C_6$ aminoalkyl, or $COR^A$. See, Scheme 2.

Scheme 2

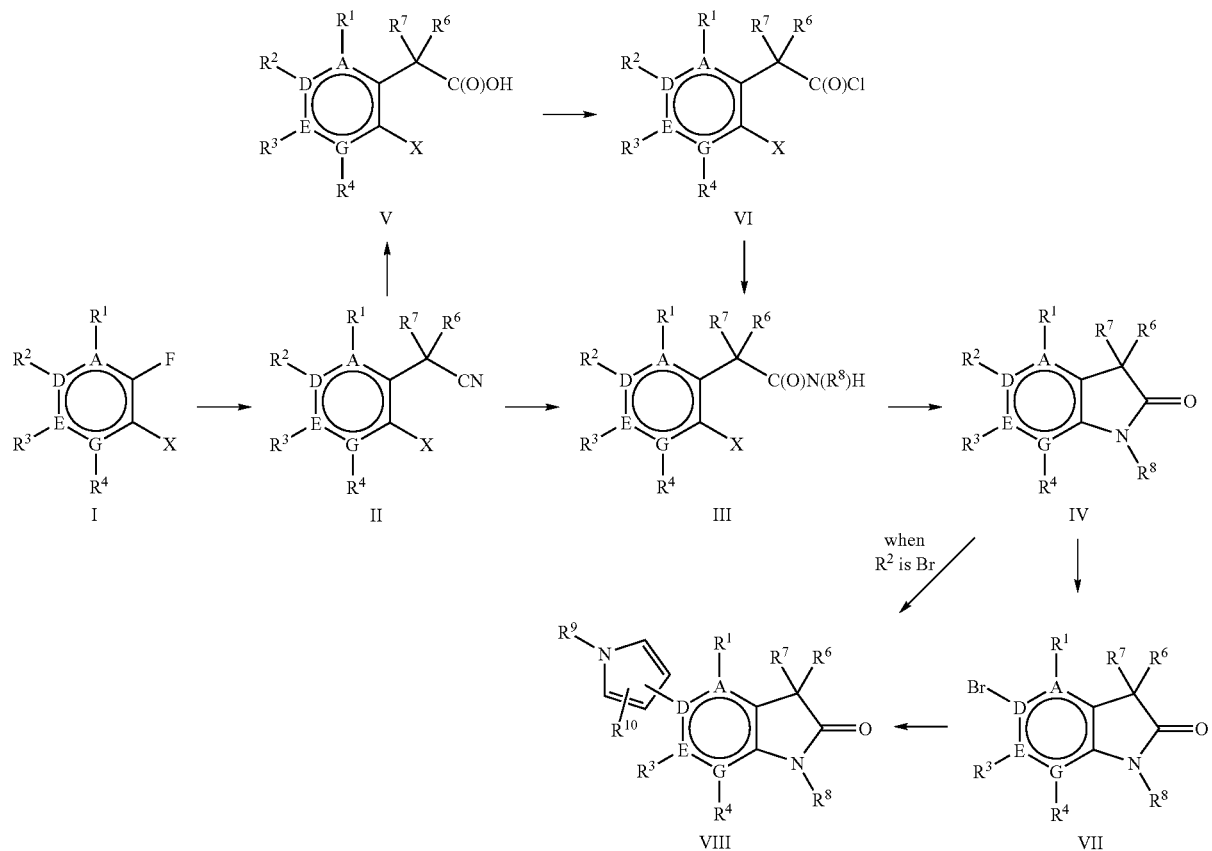

This method includes substituting a fluoroarene with a secondary nitrile to form a nitrile compound II of the structure:

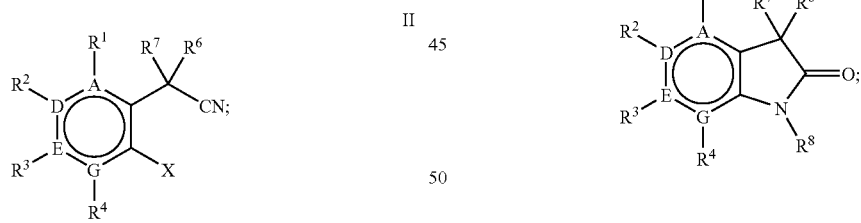

wherein, $R_2$ is a leaving group such as halogen, $OSO_2CF_3$, or $N_2^+$; converting nitrile II to amide III of the structure:

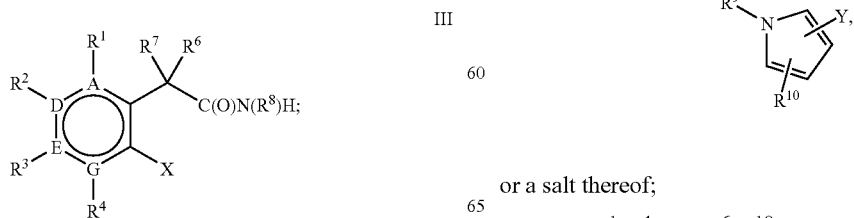

cyclizing amide III to oxindole IV of the following structure:

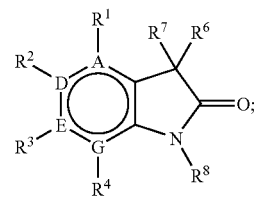

and coupling oxindole IV with a pyrrole of the structure:

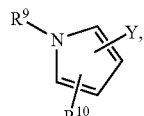

or a salt thereof;

wherein, $R^1$-$R^4$ and $R^6$-$R^{10}$ are defined above and Y is a leaving group. In one example, the pyrrole is of the structure:

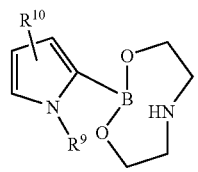

In another example, the pyrrole is a cyanopyrrole. In a further example, the pyrrole is of the structure:

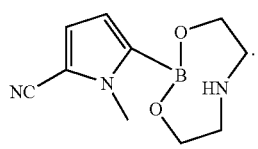

If $R^2$ is a halogen other than bromine, or triflate, oxindole IV can first be brominated at the 5-position to form the bromooxindole compound VII, which is thereby reacted with the pyrrole noted above to form the pyrrole oxindole VIII.

The term "leaving group" as used herein refers to any substituent that is displaced upon the reaction with another reagent. There are a large number of leaving groups that can be utilized to form the 5-pyrrole-3,3-oxindole compounds and include, without limitation, boron-containing leaving groups such as those described in US Patent Application Publication No. US-2005-0272702-A1, which is hereby incorporated by reference. Desirably, the leaving group is the following:

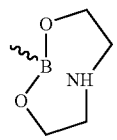

In one embodiment, the oxindole compound prepared is of the following structure:

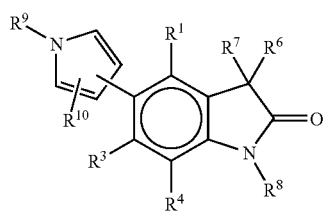

In a further embodiment, a method for preparing 5-(7-fluoro-3,3-dimethyl-2-oxo-2,3-dihydro-1H-indol-5-yl)-1-methyl-1H-pyrrole-2-carbonitrile is provided and includes substituting a fluoroarene with a secondary nitrile to form a compound of the structure:

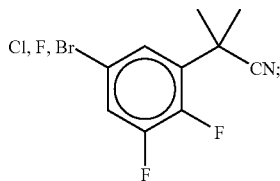

converting the nitrile to an amide of the structure:

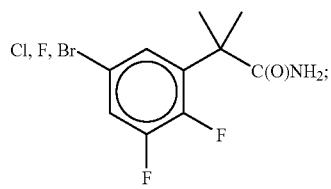

cyclizing the amide to an oxindole of the following structure:

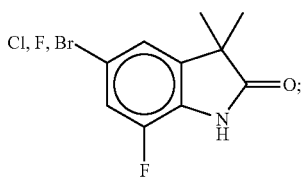

and coupling the oxindole with a 1-methyl-5-cyano-2-pyrrole compound.

In another embodiment, a method for preparing 5-(7-fluoro-3,3-dimethyl-2-oxo-2,3-dihydro-1H-indol-5-yl)-1-methyl-1H-pyrrole-2-carbonitrile is provided and includes substituting a fluoroarene with a secondary nitrile to form a compound of the structure:

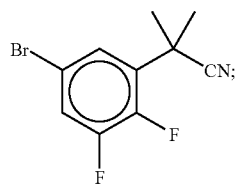

converting the nitrile an amide of the structure:

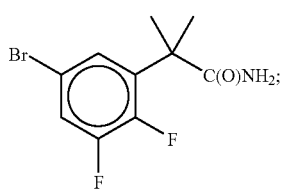

cyclizing the amide to an oxindole of the following structure:

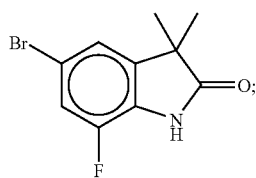

and coupling the oxindole with a 1-methyl-5-cyano-2-pyrrole compound.

The 1-methyl-5-cyano-2-pyrrole compound can be a boronate salt, borinate salt, boronic ester, borinic ester, boronic acid, or borinic acid. Desirably, the 1-methyl-5-cyano-2-pyrrole is a boronic acid. More desirably, the 1-methyl-5-cyano-2-pyrrole compound is 5-[1,3,6,2]dioxazaborocan-2-yl-1-methyl-1H-pyrrole-2-carbonitrile, the preparation of which is described in US Patent Application Publication No. US-2005-0272702-A1, which is hereby incorporated by reference.

5-(7-Fluoro-3,3-dimethyl-2-oxo-2,3-dihydro-1H-indol-5-yl)-1-methyl-1H-pyrrole-2-carbonitrile can also be prepared by substituting a fluoroarene with a secondary nitrile to form a compound of the structure:

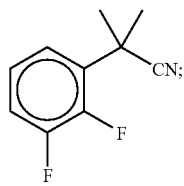

converting the nitrile to an amide of the structure:

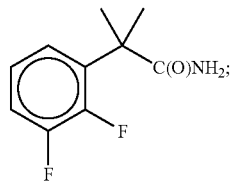

cyclizing the amide to an oxindole of the following structure:

brominating the oxindole to form a compound of the structure:

and coupling the brominated oxindole with a 1-methyl-5-cyano-2-pyrrole compound as described above.

In one embodiment, 5-(7-Fluoro-3,3-dimethyl-2-oxo-2,3-dihydro-1H-indol-5-yl)-1-methyl-1H-pyrrole-2-carbonitrile is prepared according to the sequence of steps provided in Scheme 3.

Scheme 3

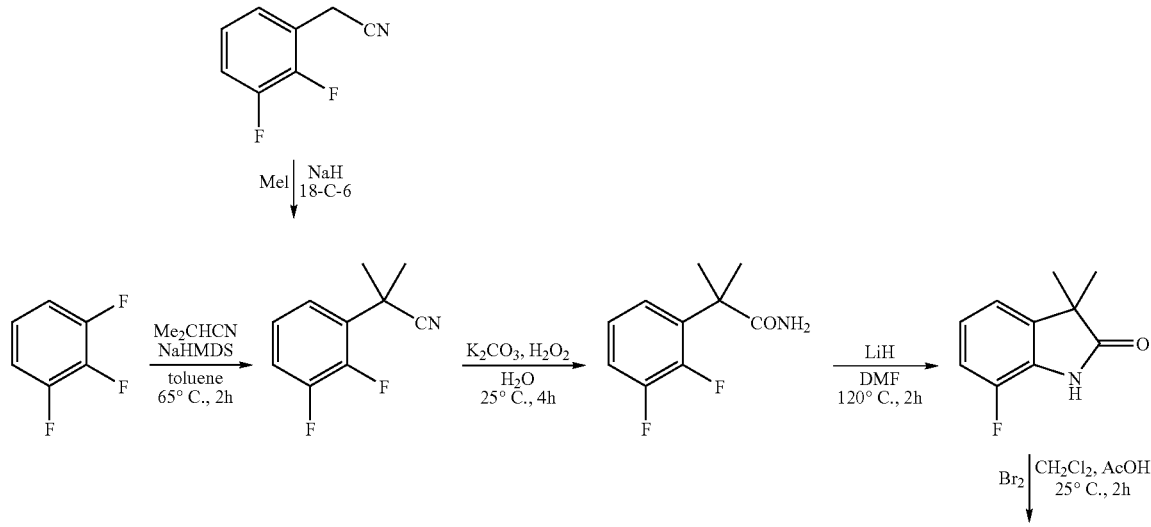

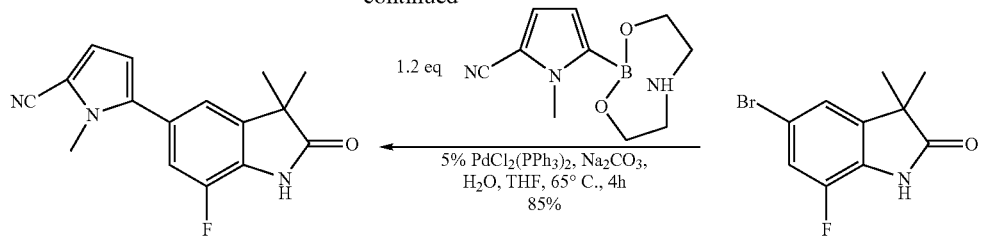

In another embodiment, a method of preparing a compound of the structure is also provided:

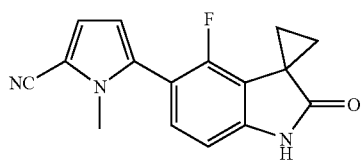

wherein said method includes:

substituting a fluoroarene with a secondary nitrile to form a compound of the structure:

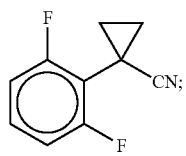

converting the nitrile to an amide of the structure:

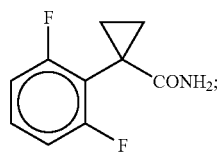

cyclizing the amide to an oxindole of the following structure:

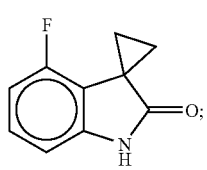

brominating the oxindole to form a compound of the structure:

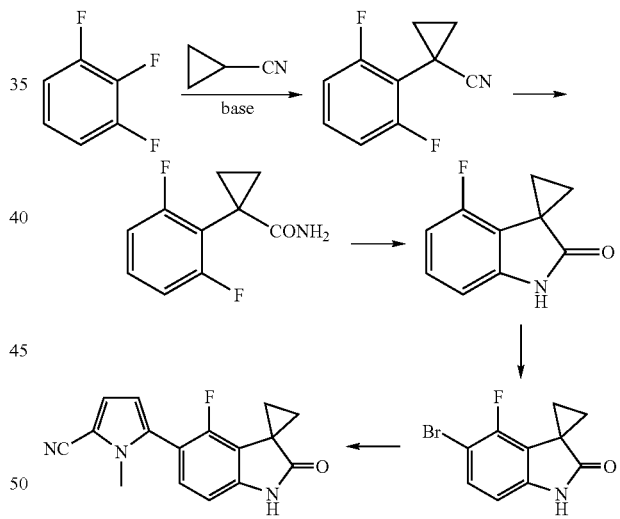

and coupling the brominated oxindole with a 1-methyl-5-cyano-2-pyrrole compound to form the product described above. See, Scheme 4.

In still another embodiment, a method of preparing a compound of the structure is provided:

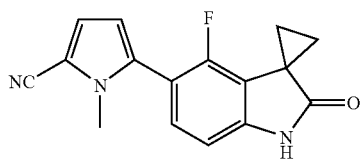

wherein the method includes alkylating a benzylnitrile to form a compound of the structure:

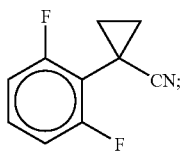

converting the nitrile to an amide of the structure:

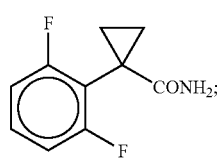

cyclizing the amide to an oxindole of the following structure:

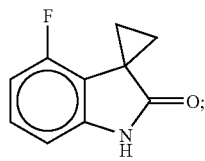

brominating the oxindole to form a compound of the structure:

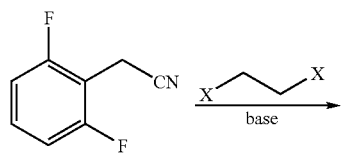

and coupling the brominated oxindole with a 1-methyl-5-cyano-2-pyrrole compound to form the product described above. See, Scheme 5.

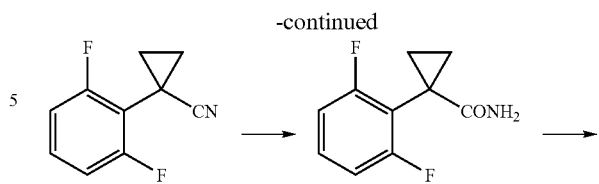

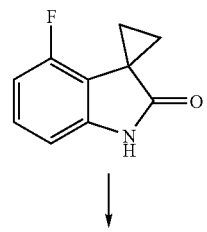

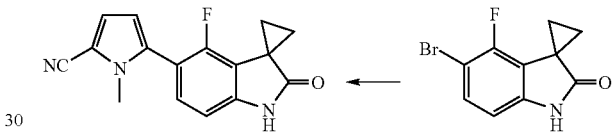

In a further embodiment, methods of preparing thio-oxindole compounds are provided. These thio-oxindole compounds can be prepared directly from the oxindoles prepared as described above using thionating agents known in the art. Suitable thionating agents include, without limitation, 2,4-bis(4-methoxyphenyl)-1,3-dithia-2,4-diphosphetane-2,4-disulfide (Lawesson's reagent) or phosphorus pentasulfide.

In yet another embodiment, methods for preparing thio-oxindole compounds are provided and include preparing nitrile II as described above; converting nitrile II to amide III; converting amide III to thioamide IX; and cyclizing thioamide IX to thio-oxindole X. See, Scheme 6.

In still a further embodiment, methods for preparing iminobenzo[b]thiophene compounds are provided and include preparing nitrile II as described above; converting nitrile II to amide III; converting amide III to thioamide IX; and cyclizing thioamide IX to iminobenzo[b]thiophene XI. See, Scheme 6.

Several reagents can be utilized to cyclize the thioamide to the iminobenzo[b]thiophene and include, without limitation, bases such as those described above or weaker bases thereof which could readily be selected by one of skill in the art.

In yet another embodiment, methods for preparing benzo[b]thiophenone compounds are provided and include preparing nitrile II as described above; converting nitrile II to amide III; converting amide III to thioamide IX; cyclizing thioamide IX to iminobenzo[b]thiophene XI; and converting iminobenzo[b]thiophene XI to benzo[b]thioophenone XII. See, Scheme 6.

Scheme 6

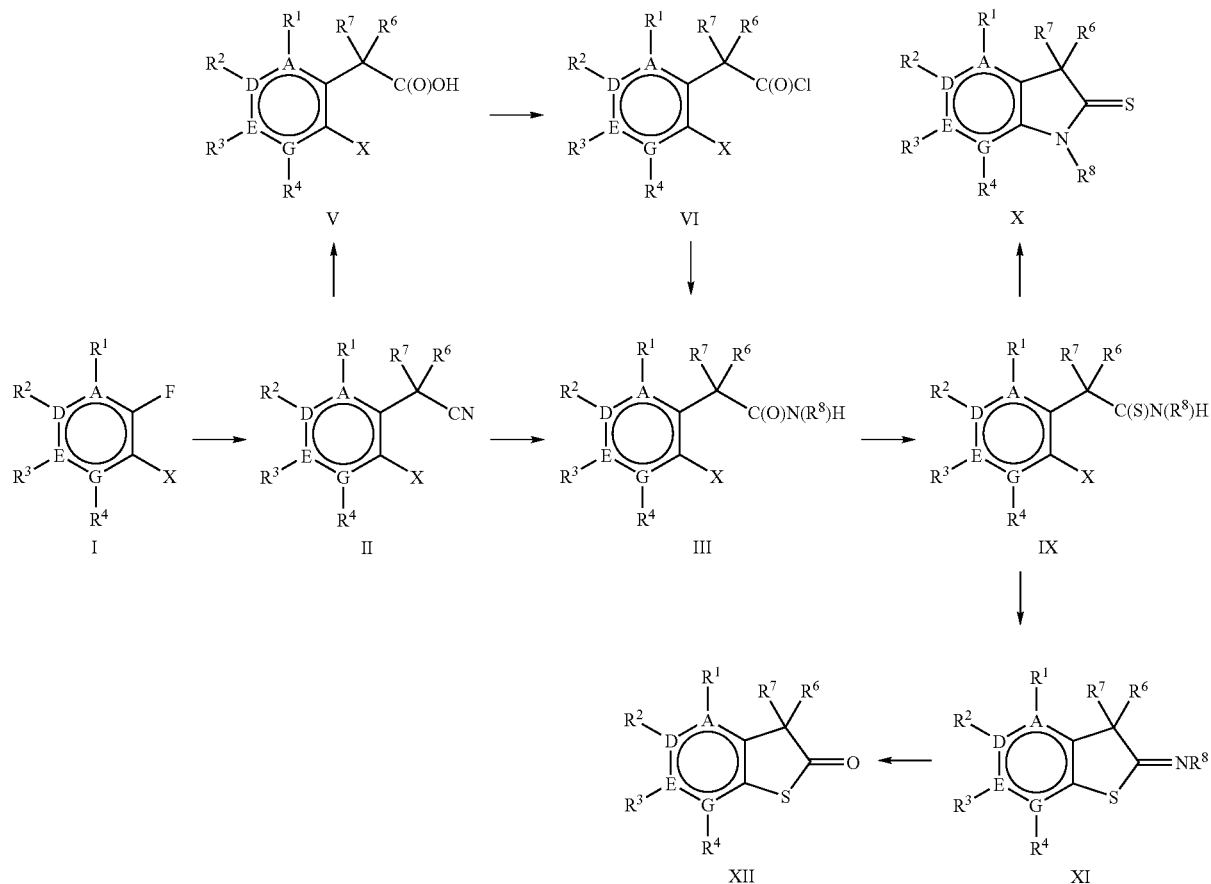

Also provided is a method for preparing thio-oxindole compounds including converting fluoroarene I to nitrile II; converting nitrile II to thioamide IX; and cyclizing thioamide IX to thio-oxindole X. See, Scheme 7.

Further provided is a method for preparing iminobenzo[b]thiophene compounds including converting fluoroarene I to nitrile II; converting nitrile II to thioamide IX; and cyclizing thioamide IX to iminobenzo[b]thiophene XI. See, Scheme 7.

A method for preparing benzo[b]thiophenone compounds are also provided and include converting fluoroarene I to nitrile II; converting nitrile II to thioamide IX; cyclizing thioamide IX to iminobenzo[b]thiophene XI; and converting iminobenzo[b]thiophene XI to benzo[b]thiophenone XII. See, Scheme 7.

Scheme 7

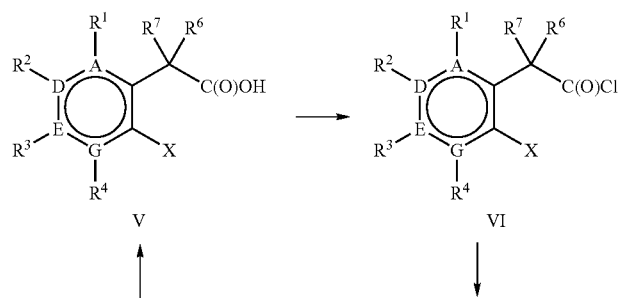

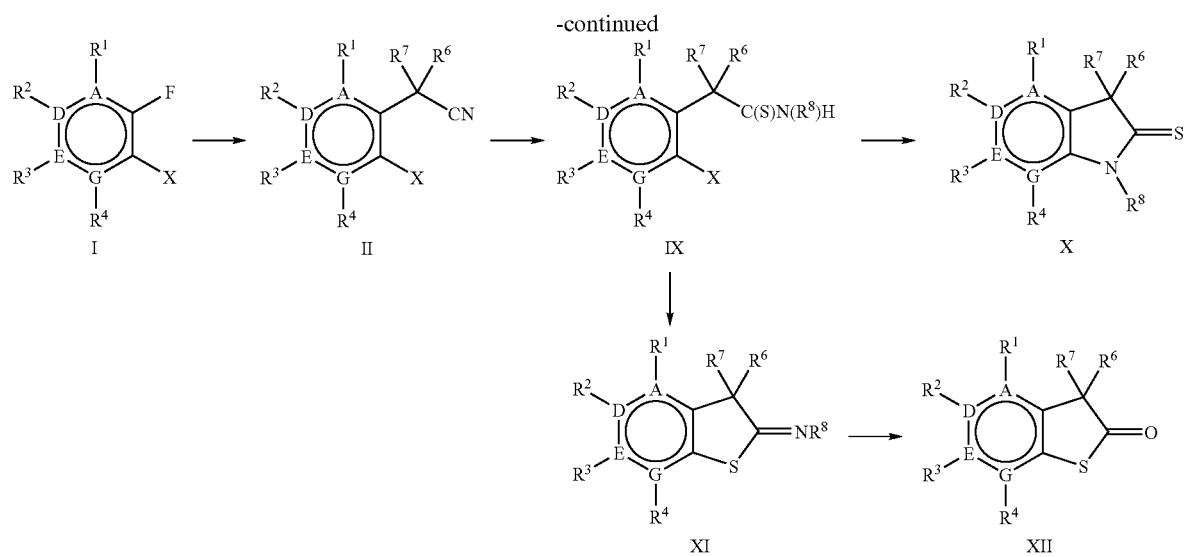

The nitrile II can be converted to a thioamide using techniques described in the art and as described in US Patent Application Publication No. US-2005-0227971-A1, which is hereby incorporated by reference. Typically, the nitrile is converted to a thioamide using a base and a sulfur-containing agent (See, R. Shabana, H. J. Meyer, S.-O. Lawesson *Phosphorus and Sulfur* 1985, 25, 297). The sulfur-containing agent includes, without limitation, a dialkyldithiophosphate, a diaryldithiophosphate, hydrogen sulfide ($H_2S$), 2,4-bis(4-methoxyphenyl)-1,3-dithia-2,4-diphosphetane-2,4-disulfide (Lawesson's reagent), or phosphorus pentasulfide. Desirably, the sulfur-containing agent is a dialkyldithiophosphate or diaryldithiophosphate, and more desirably diethyldithiophosphate. The base is typically an amine. Desirably, the amine is an alkylated amine including N,N-diisopropylethylamine (Hünig's base), triethylamine, or pyridine, among others.

The iminobenzo[b]thiophene VI can then be converted to the corresponding benzo[b]thiophenone XII using reagents known to those of skill in art. Specifically, the imine moiety of the benzo[b]thiophene can be protonated and thereby hydrolyzed to a carbonyl. In one example, when $R^8$ is H, the imine moiety can be protonated with a strong acid such as hydrochloric acid, hydrosulfuric acid, and triflic acid, among others, and thereby hydrolyzed to a carbonyl group to provide a benzo[b]thiophenone XII.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Product Distribution in the Reaction of 1,2,3-trifluorobenzene and 2-methylpropionitrile in the Presence of Various Bases The reaction tubes of Mettler Toledo MiniBlock™ were independently charged with 1,2,3-trifluorobenzene (1.32 g, 0.01 mol). A solution of 2-methylpropionitrile (14 g) in toluene (160 mL) was prepared and 8.5 mL (containing 0.01 mol of 2-methylpropionitrile) was dispensed to each tube. Equimolar amounts of the bases in Table 1 were then added dropwise at ambient temperature. The mixtures were heated to 65° C. over 3 hours, cooled to ambient temperature and quenched with 5% hydrochloric acid (6 mL each). The organic phases were separated and solvents evaporated. The residues were analyzed by GC/MS as solutions in acetonitrile.

TABLE 1

| | | Normalized (area %) product distribution | | |
|---|---|---|---|---|
| Base | Conc. (M)/ Solvent | 2-(2,3-Difluorophenyl)-2-methylpropionitrile (Isomer A) | 2-(2,6-Difluorophenyl)-2-methylpropionitrile (Isomer B) | 2-[3-(Cyano-dimethyl-methyl)-2-fluorophenyl]-2-methylpropionitrile (Isomer C) |
| KHMDS | 0.5/toluene | 33 | 23 | 44 |
| NaHMDS | 0.6/toluene | 55 | 18 | 27 |
| NaHMDS | 1/THF | 62 | 19 | 19 |
| LiHMDS | 1/THF | 70 | 15 | 15 |
| LDA | 2/heptane, THF EtPh | 64 | 16 | 20 |

TABLE 1-continued

| Base | Conc. (M)/ Solvent | 2-(2,3-Difluorophenyl)-2-methylpropionitrile (Isomer A) | 2-(2,6-Difluorophenyl)-2-methylpropionitrile (Isomer B) | 2-[3-(Cyano-dimethyl-methyl)-2-fluorophenyl]-2-methylpropionitrile (Isomer C) |
|---|---|---|---|---|
| | | Normalized (area %) product distribution | | |
| i-PrMgCl | 2/THF | 79 | 17 | 3 |
| MeMgBr | 1.4/toluene, THF | 86[a] | 14 | 0 |
| VinylMgBr | 1/THF | 89[a] | 11 | 0 |
| t-PentOK | 1.7/toluene | [b] | — | — |
| t-BuOK | 1/THF | [c] | — | — |
| MeLi | 1.5/ether | [d] | — | — |
| HexLi | 2.3/hexane | [e] | — | — |
| NaH | — | decomposed | — | — |
| TMG | — | decomposed | — | — |

[a] The reaction mixture contained a number of side-products.
[b] 75 and 16% of the respective tert-pentoxyethers and minute amounts of the desired nitriles.
[c] 66 and 22% of the respective tert-butoxyethers and minute amounts of the desired nitriles.
[d] 33.5% isomer A, 5.2% isomer B, in addition to a number of side-products.
[e] 5.5% isomer A, 0.7% isomer B, in addition to a number of side-products.

These data illustrate isomer A could be isolated as the major product, particularly when using the Grignard bases.

Example 2

Product Distribution in the Reaction of 1,2,3-trifluorobenzene and 2-methylpropionitrile in the Presence of isopropylmagnesium chloride in Various Solvents This example was performed as described in Example 1, whereby seven samples were prepared by dissolving 1,2,3-trifluorobenzene (1.32 g, 0.01 mol) and 2-methylpropionitrile (0.9 mL, 0.69 g, 0.01 mol) in the solvent (8 mL each) noted in Table 2. Isopropylmagnesium chloride (2M in THF, 5 mL each) was independently added dropwise to these mixtures. The mixtures were then heated to 35° C. over 3 hours, cooled to ambient temperature and quenched with 5% HCl (6 mL). The reaction mixture containing triethylamine was additionally treated with concentrated hydrochloric acid. The organic phases were separated and the solvents were evaporated. The residues were analyzed by GC/MS as solutions in acetonitrile.

TABLE 2

| Solvent | Isomer A | Isomer B | Isomer C |
|---|---|---|---|
| | Normalized (area %) product distribution | | |
| Tetrahydrofuran | 83.0 | 16.5 | 0.4 |
| Dioxane | 83.7 | 16.3 | 0 |
| 1,2-Dimethoxyethane | 85.9 | 14.1 | 0 |
| Ethyl ether | 84.8 | 15.2 | 0 |
| Triethylamine | 80.2 | 16.0 | 3.7 |
| Dichloromethane[a] | 85.8 | 14.2 | 0 |
| Methyl tert-butyl ether | 84.2 | 15.6 | 0.1 |

[a] The reaction mixture contained numerous side-products.

These data illustrate that the ether solvents were most useful in isolating the isomer A compound as the major product.

Example 3

Product Distribution in the Reaction of 1,2,3-trifluorobenzene and 2-methylpropionitrile in the Presence of isopropylmagnesium chloride at Various Temperatures Three flasks were equipped with a thermocouple, condenser with a nitrogen inlet, and a magnetic stirring bar. 1,2,3-trifluorobenzene (1.32 g, 0.01 mol) and 2-methylpropionitrile (0.9 mL, 0.69 g, 0.01 mol) were added to each flask and thereby dissolved in THF (8 mL). The contents of the first flask were cooled to −25° C.; the contents of the second flask were cooled to 0° C.; and the contents of the third flask were heated to 60° C. Isopropylmagnesium chloride (2M in THF, 5 mL each) was added dropwise to each solution maintaining the respective reaction temperatures. After 2 hours, the reactions were quenched with 5% HCl (6 mL each). The organic phases were separated and the solvent was evaporated. The residues were analyzed by GC/MS as solutions in acetonitrile. See, Table 3.

TABLE 3

| Reaction temperature (° C.) | Isomer A | Isomer B | Isomer C |
|---|---|---|---|
| | Normalized (area %) product distribution | | |
| −25 | 88.0 | 12.0 | 0 |
| 0 | 85.5 | 14.5 | 0 |
| 60 | 82.2 | 17.2 | 0.14 |

These data illustrate that temperature has a minimal effect on the isomer distribution. However, the use of a lower temperature provides a higher amount of Isomer A.

Example 4

Reaction of haloarenes and 2-methylpropionitrile in the Presence of Various Bases in THF The reaction tubes of Mettler Toledo MiniBlock™ were independently charged with the haloarenes (0.01 mol) identified below and a solution of 2-methylpropionitrile in THF (8.5 mL, 0.01 mol) which was prepared from the nitrile (14 g) and THF (160 mL). An equimolar amount of the base (0.01 mol) was independently added to each tube dropwise at ambient temperature. The reaction mixtures were heated to 65° C. over 1 hour, cooled to ambient temperature and quenched with 5% HCl (6 mL). The organic phases were separated and the solvents were evaporated. The crude product mixtures were examined using gas chromatography (GC)/mass spectroscopy (MS) and proton nuclear magnetic resonance ($^1$H-NMR).

A.

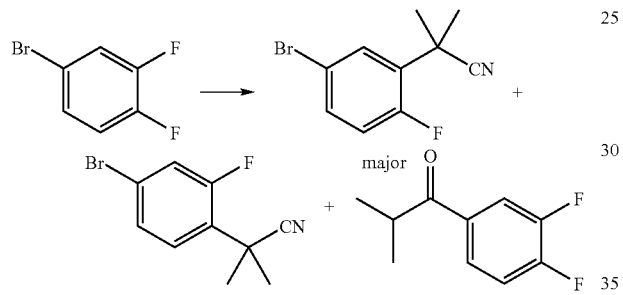

haloarene: 1-bromo-3,4-difluorobenzene;
base: isopropylmagnesium chloride (2M in THF);
0.642 grams of products:
(i) 2-(5-bromo-2-fluorophenyl)-2-methylpropionitrile: major, 73.1% by GC/MS;
$^1$H-NMR (CDCl$_3$): δ 7.59 (H6, dd, 6.8, 2.4 Hz), 7.44 (H4, ddd, 8.6, 4.4, 2.4), 7.01 (H3, dd, 11.2, 8.8), 1.785 (s, 6H, CH$_3$);
(ii) 2-(4-bromo-2-fluorophenyl)-2-methylpropionitrile: minor, 9.1% by GC/MS;
(iii) 1-(3,4-difluorophenyl)-2-methylpropan-1-one: minor, 15% by GC/MS.

B.

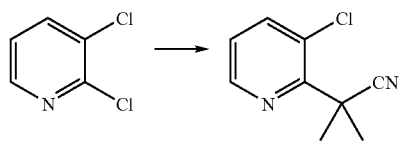

haloarene: 2,3-dichloropyridine;
base: isopropylmagnesium chloride (2M in THF);
1.237 grams of:
(i) 2-(3-chloropyridin-2-yl)-2-methylpropionitrile 50% yield as evidenced by $^1$H-NMR;
Structure assignment was based on GC/MS and $^1$H-NMR data (CDCl$_3$): δ 8.48 (H6, dd, 4.4, 1.6 Hz), 7.76 (H4, dd, 8.0, 1.6), 7.29 (H5, dd, 8.0, 4.8), 1.87 (s, 6H, CH$_3$); $^{13}$C-NMR data (CDCl$_3$): δ 154.20 ppm C2, 147.05 C6, 139.45 C4, 131.03 C3, 124.37 C5, 123.10 CN, 38.59 C, 26.59 CH$_3$; and
(ii) residual haloarene: 50%.

C.

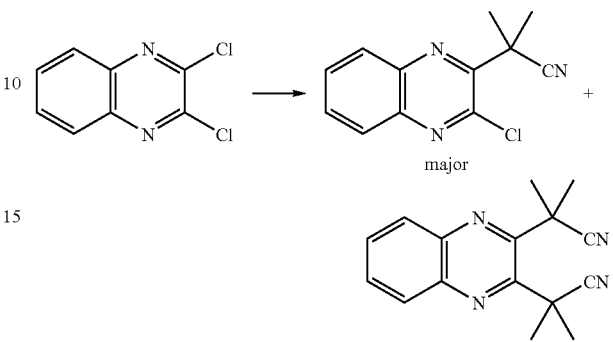

haloarene: 2,3-dichloroquinoxaline;
base: potassium hexamethyldisilazide (0.5M in toluene);
0.988 grams of:
(i) 2-(3-chloroquinoxalin-2-yl)-2-methylpropionitrile: 95.9% yield as evidenced by GC/MS);
$^1$H-NMR (DMSO-d$_6$): δ 8.19-8.15 (m, 1H), 8.13-8.10 (m, 1H), 8.01-7.96 (m, 2H), 1.94 (s, 6H);
(ii) residual haloarene: 2.82%; and
(iii) 2-[3-(cyanodimethylmethyl)-quinoxalin-2-yl]-2-methylpropionitrile: 1.32% yield.

D.

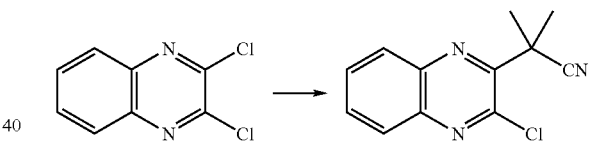

haloarene: 2,3-dichloroquinoxaline;
base: isopropylmagnesium chloride 1 (2M in THF);
product: 2-(3-chloroquinoxalin-2-yl)-2-methylpropionitrile (38.1% by GC/MS) and residual haloarene (61.1%).

E.

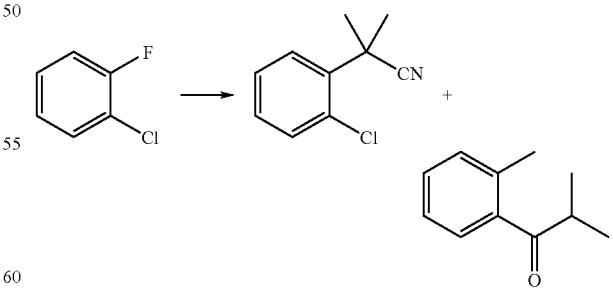

haloarene: 1-chloro-2-fluorobenzene;
base: o-tolylmagnesium chloride (1M in THF);
products: 2-(2-chlorophenyl)-2-methylpropionitrile (29.6% by GC/MS); residual haloarene (47.9%); and 2'-methylisobutyrophenone (12.7%)

F.

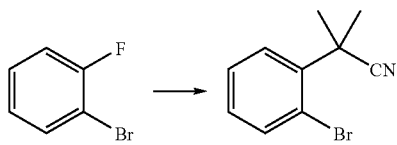

haloarene: 1-bromo-2-fluorobenzene;

base: sodium hexamethyldisilazide (1M in THF);

product: 2-(2-bromophenyl)-2-methylpropionitrile (5.2% by GC/MS) and residual haloarene (76.8%)

G.

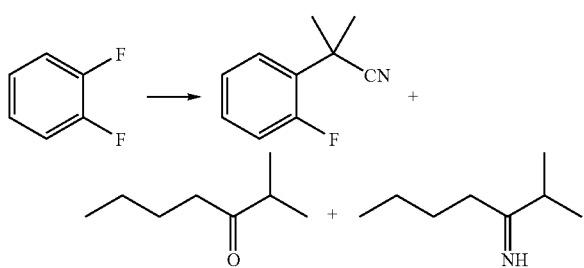

substrate: 1,2-difluorobenzene;

base: dibutylmagnesium chloride (1M in heptane);

products: 2-(2-fluorophenyl)-2-methylpropionitrile (2.8% by GC/MS); 2-methylheptan-3-one (29.0%); and its imine analog (57.8%)

Example 5

Reaction of 1,2-difluorobenzene with Various Secondary nitriles in the Presence of isopropylmagnesium chloride in THF Mettler Toledo MiniBlock™ reaction vessels were independently charged with 1,2-difluorobenzene (0.01 mol), a nitrile (0.01 mol) identified below, and THF (8 mL). Isopropylmagnesium chloride (2M in THF, 5 mL each) was added dropwise at ambient temperature to each vessel. The reaction mixtures were heated to 65° C. over 4 hours, cooled to ambient temperature and quenched with 5% HCl (6 mL). The organic phases were separated and the solvents were evaporated. The crude product mixtures were examined using GC/MS and $^1$H-NMR.

A.

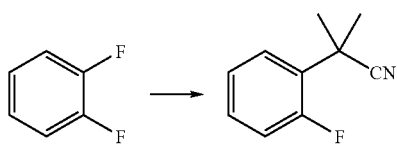

nitrile: 2-methylpropionitrile;

0.637 grams of 2-(2-fluorophenyl)-2-methylpropionitrile (97.9% by GC/MS). $^1$H-NMR (DMSO-$d_6$): δ 7.52-7.42 (m, 2H), 7.34-7.25 (m, 2H), 1.74 (s, 6H).

B.

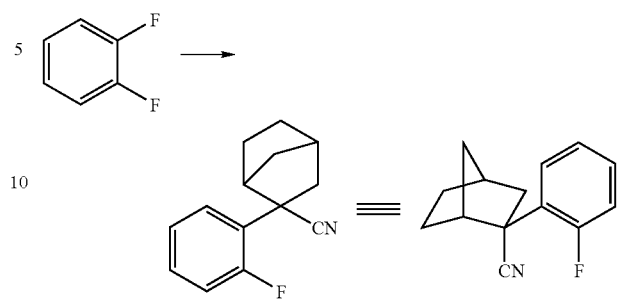

nitrile: 2-norbornanecarbonitrile;

1.570 grams of the following products:

(i) exo-2-(2-fluorophenyl)bicyclo[2.2.1]heptane-2-carbonitrile (95.1% by GC/MS);

(ii) endo-2-(2-fluorophenyl)bicyclo[2.2.1]heptane-2-carbonitrile (0.73%); and (iii) 1-bicyclo[2.2.1]hept-2-yl-2-methyl-propanone (1.65%).

The structure was assigned based on $^1$H-NMR and literature data (I. Fleming, et al, *J. Chem. Soc., Perkin Trans. 1*, 1986, 349; S. Caron, et al, *J. Am. Chem. Soc.* 2000, 122, 712).

C.

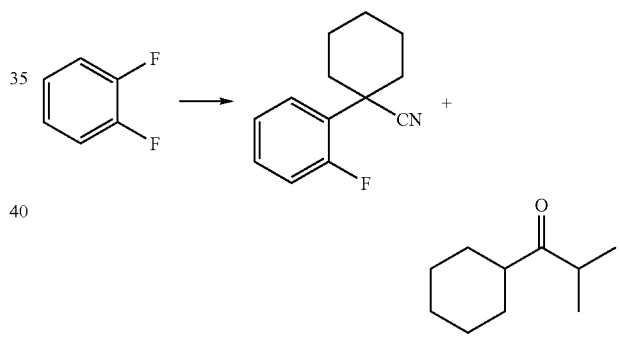

nitrile: cyclohexanecarbonitrile;

products: 1-(2-fluorophenyl)cyclohexanecarbonitrile (43.3% by GC/MS) and 1-cyclohexyl-2-methylpropanone (33.2%)

Example 6

Preparation of 2-(2,3-difluorophenyl)-2-methylpropionitrile and 2-(2,6-difluorophenyl)-2-methylpropionitrile

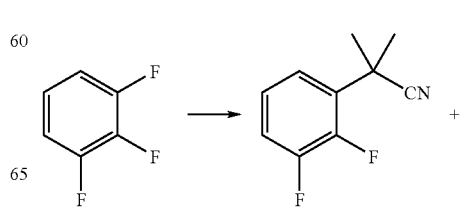

-continued

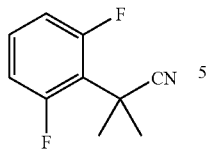

1M sodium hexamethyldisilazide in tetrahydrofuran (40 mL) was added in portions to a stirred solution of 1,2,3-trifluorobenzene (5.03 g) and 2-methylpropionitrile (2.81 g) in toluene (30 mL). The reaction mixture was heated to 68° C. for 3 hours, additionally stirred at ambient temperature overnight, and quenched into 5% HCl. The organic phase was separated and washed with water and brine. Evaporation of the solvent gave an oil (5.99 g) containing a 76:24 ratio of isomers: 2-(2,3-difluorophenyl)-2-methylpropionitrile (65.4% by GC/MS, RT 6.20 min.); 2-(2,6-difluorophenyl)-2-methylpropionitrile (20.3%, RT 6.78 min.); and 2-[3-(cyanodimethylmethyl)-2-fluorophenyl]-2-methylpropionitrile (14.1%, RT 10.4 min.). $^{1}$H-NMR (DMSO-d$_6$): major CH$_3$ singlet at 1.76 ppm and a minor singlet at 1.83 ppm.

Example 7

Hydrolysis of a Crude Mixture of 2-(2,3-difluorophenyl)-2-methylpropionitrile and 2-(2,6-difluorophenyl)-2-methylpropionitrile

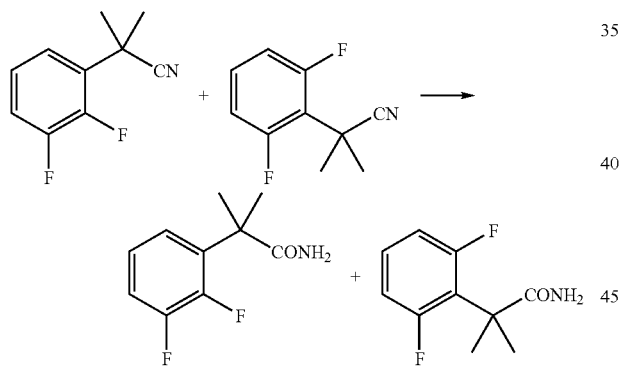

A sample of crude 2-(2,3-difluorophenyl)-2-methylpropionitrile and 2-(2,6-difluorophenyl)-2-methylpropionitrile (4.12 g) was dissolved in methanol (10 mL) and water (3 mL). Tetrabutylammonium hydrogensulfate (25 mg) and sodium percarbonate (1.20 g) were added to the methanol solution at ambient temperature, followed by a dropwise addition of 50% hydrogen peroxide (3 mL) within 5 hours. The stirring was continued for 40 hours, after which the reaction mixture was extracted with ethyl acetate and water. The organic phase was dried over anhydrous magnesium sulfate, filtered and evaporated to provide an oil, which solidified upon evaporation with hexane to give a waxy solid (4.80 g).

GC/MS showed two m/z 199 isomers: 18.5 and 63.6% (23:77 ratio; RT 9.05 and 9.27 min., respectively). $^{1}$H-NMR (DMSO-d$_6$) showed a major singlet at 1.60 ppm (CH$_3$) and two major CON$\underline{H}_2$ signals at 5.98 and 5.45 ppm. These resonances were attributed to 2-(2,3-difluorophenyl)isobutyramide. Minor CON$\underline{H}_2$ signals at 6.43 and 5.73 ppm were attributed to 2-(2,6-difluorophenyl)isobutyramide.

Example 8

Thionation of a Crude Mixture of 2-(2,3-difluorophenyl)isobutyramide and 2-(2,6-difluorophenyl) isobutyramide

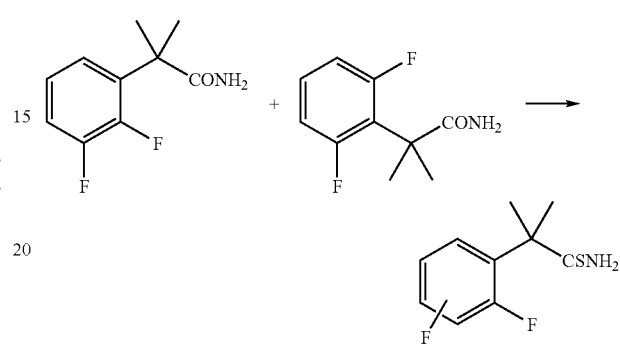

A crude sample of 2-(2,3-difluorophenyl)isobutyramide and 2-(2,6-difluorophenyl)isobutyramide (1.86 g) was heated to 84° C. with Lawesson's reagent (2.0 g) in 1,2-dimethoxyethane (30 mL) for 16 hours. The clear, light-orange solution was cooled to ambient temperature and poured into water. The precipitated orange oil was stirred overnight to form sticky, pale yellow oil. The pale yellow oil was extracted with chloroform (3×), the organic extracts washed with water (2×), and dried over anhydrous magnesium sulfate. Filtration followed by evaporation gave a light-brown solid (2.37 g). GC/MS showed m/z 215 product (RT 11.31 min.) along with three other by-products.

Example 9

Cyclization of a Mixture of 2-(2,3-difluorophenyl)isobutyramide and 2-(2,6-difluorophenyl)isobutyramide to a Mixture of 7-fluoro-3,3-dimethyl-1,3-dihydroindol-2-one and 4-fluoro-3,3-dimethyl-1,3-dihydroindol-2-one, Respectively

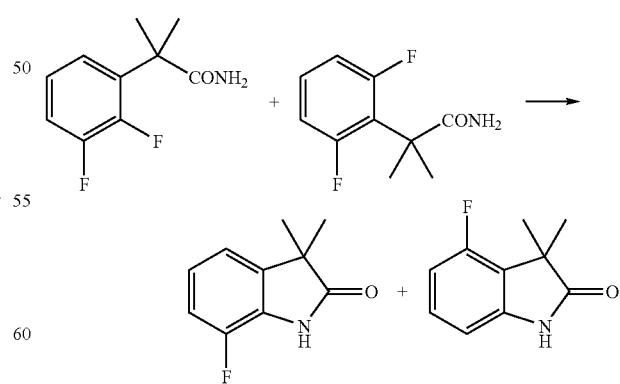

A crude sample of 2-(2,3-difluorophenyl)isobutyramide and 2-(2,6-difluorophenyl)isobutyramide (0.548 g) was dissolved in dimethylformamide (DMF-3 mL), treated with a small portion of lithium hydride suspended in DMF (1 mL), and heated gradually to 120° C. over 7 hours. Upon cooling, the mixture was quenched with 5% HCl and ethyl acetate. The quenched mixture was extracted twice with ethyl acetate and the combined organic phases were back-extracted with brine (3×). After drying over anhydrous magnesium sulfate, filtration and evaporation, an oil (0.373 g) was obtained that solidified on standing.

Analysis by GC/MS showed two m/z 179 isomers in 81:19 ratio (8.23 and 8.98 min., respectively). $^1$H-NMR (DMSO-$d_6$): 1.34 and 1.27 ppm (s, $CH_3$; minor and major, respectively). The major isomer was identified as 7-fluoro-3,3-dimethyl-1,3-dihydroindol-2-one based on GC/MS, LC and $^1$H-NMR data comparison with an authentic sample, prepared by an independent route.

Example 10

Basis Hydrolysis of 2-(2-fluorophenyl)-2-methylpropionitrile

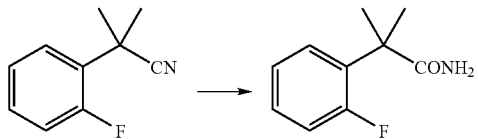

2-(2-Fluorophenyl)-2-methylpropionitrile (0.211 g) was magnetically stirred with aqueous solutions of 5N sodium hydroxide (2 mL), 55% tetrabutylammonium hydrogensulfate (0.1 mL) and 30% hydrogen peroxide (3 mL) for 22 hours. The reaction mixture was diluted with toluene and extracted. The aqueous phase was neutralized with 5% hydrochloric acid and extracted twice with ethyl acetate. The combined organic extracts were washed with water, then brine, and dried over anhydrous magnesium sulfate. Filtration and evaporation gave 2-(2-fluorophenyl)isobutyramide as a pale-green oil that solidified on standing (0.173 g). GC/MS: m/z 181 (RT 9.80 min.). $^1$H-NMR (DMSO-$d_6$): 7.39-7.27 (m, 2H), 7.19-7.07 (m, 2H), 6.83 and 6.78 (2 s, $CONH_2$), 1.43 (s, 6H)

Example 11

Acidic Hydrolysis of 2-(3-chloropyridin-2-yl)-2-methylpropionitrile with Concomitant Purification

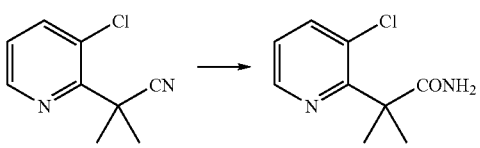

A crude mixture of 2-(3-chloropyridin-2-yl)-2-methylpropionitrile and 2,3-dichloropyridine (0.171 g) was dissolved in concentrated hydrochloric acid (4 mL) and the solution was heated to 90-95° C. for 5.5 hours. Upon cooling, it was diluted with water and extracted twice with dichloromethane. The aqueous phase was basified with sodium hydroxide (with cooling) to pH of 8 and extracted twice with dichloromethane. The organic extracts were washed with water and dried over anhydrous magnesium sulfate. Filtration and evaporation gave 2-(3-chloropyridin-2-yl)isobutyramide (64 mg). $^1$H-NMR (DMSO-$d_6$): δ 8.48 (dd, 4.6, 1.5 Hz), 7.83 (dd, 7.95, 1.5), 7.325 (dd, 7.95, 4.6), 6.97 and 6.93 (2 s, $CONH_2$), 1.50 (s, 6H).

The reaction illustrated that acidic hydrolysis was the preferred method of hydrolysis since the protonation solubilizes the mixture of pyridines in aqueous medium.

Further, since the $^1$H-NMR spectrum showed minimal by-products, it was hypothesized that the 2,3-dichloropyridine by-product (which was produced in Example 4) was hydrolyzed to 2-hydroxy-3-chloropyridine which formed a water-soluble salt (phenolate) upon treatment with NaOH. Thus, only the desired amide product was extracted into the organic phase.

Example 12

Hydrolysis of exo-2-(2-fluorophenyl)bicyclo[2.2.1]heptane-2-carbonitrile

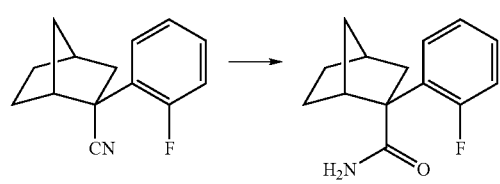

The crude nitrile (1.51 g) noted above was heated to 75° C. with concentrated sulfuric acid (2 mL) and water (0.5 mL) for 17 hours. The reaction mixture was diluted with water and extracted twice with ethyl acetate. The organic extracts were washed twice with brine and the solvent evaporated to give a pale-brown solid (1.91 g), 2-(2-fluorophenyl)bicyclo[2.2.1]heptane-2-carboxylic acid amide. $^1$H-NMR (DMSO-$d_6$) showed amide protons at 6.81 and 6.42 ppm. GC/MS: m/z 233 (purity 4.9%, RT 12.54 min.).

Example 13

Preparation of 1-(2,6-difluorophenyl)cyclopropanecarboxylic acid amide

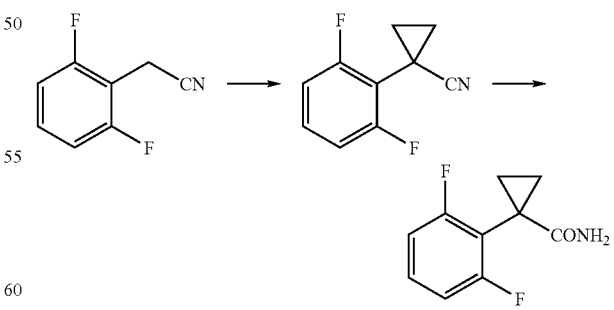

1-(2,6-Difluorophenyl)cyclopropanecarbonitrile was prepared as described in U.S. Pat. No. 4,859,232 by alkylation of 2,6-difluorophenylacetonitrile with 1,2-dibromoethane in 50% sodium hydroxide in the presence of catalytic amounts of tetrabutylammonium bromide (quantitative yield; GC/MS:

m/z 179, RT 8.24 min.; $^1$H-NMR (DMSO-d$_6$): δ 7.58-7.48 (m, 1H), 7.24-7.16 (m, 2H), 1.84-1.79 (m, 2H), 1.46-1.41 (m, 2H)).

1-(2,6-Difluorophenyl)cyclopropanecarbonitrile was also prepared by reacting 1,2,3-trifluorobenzene (2.64 g), cyclopropanecarbonitrile (1.65 g) and 0.5M potassium hexamethyldisilazide in toluene (40 mL). The isolated solid (2.99 g) contained a mixture of 1-(2,6-difluorophenyl)cyclopropanecarbonitrile (39.6% by GC/MS; RT 8.22 min.; authentic with the one prepared above), 1-(2,3-difluorophenyl)cyclopropanecarbonitrile (12.4%; RT 8.65 min.; m/z 179, 100%), two di-substituted products with m/z 226 (37.0 and 4.4%; RT 12.6 and 14.0 min., m/z 184 (100%) and 226 (100%), respectively), and a tri-substituted product with m/z 273 (6.6%; RT 16.4 min., m/z 190 (100%)).

1-(2,6-Difluorophenyl)cyclopropanecarbonitrile (5.42 g) was hydrolyzed at ambient temperature with an aqueous solutions of 5N sodium hydroxide (20 mL), 55% tetrabutylammonium hydrogensulfate (0.5 mL) and 30% hydrogen peroxide (5 mL) in toluene (5 mL) for 39 hours. The prepared semi-solid reaction mixture was diluted with ethyl acetate and the phases were separated. The aqueous phase was neutralized with 5% hydrochloric acid and extracted twice with ethyl acetate. The combined organic extracts were washed with 5% hydrochloric acid, then brine, and dried over anhydrous sodium sulfate. Filtration and evaporation gave 1-(2,6-difluorophenyl)cyclopropanecarboxylic acid amide as light-brown solid (4.98 g, 84% yield). M.p. 136.7-137.6° C. (from ethyl acetate). GC/MS: m/z 197 (purity 97.5%, RT 9.85 min.). $^1$H-NMR (DMSO-d$_6$): δ 7.43-7.34 (m, 1H), 7.10-7.01 (m, 2H), 6.96 (br s, 1H), 6.64 (br s, 1H), 1.50-1.46 (m, 2H), 1.00-0.97 (m, 2H). $^1$H-NMR (CDCl$_3$): δ 7.61-7.26 (m, 1H), 6.98-6.90 (m, 2H), 5.44 (br s, 2H), 1.79-1.74 (m, 2H), 1.17-1.12 (m, 2H). $^{13}$C-NMR (DMSO-d$_6$): 173.4, 164.2, 160.9, 130.3, 116.5, 112.1, 19.05, 15.8.

Example 14

Preparation of 2-(2-fluorophenyl)isobutyramide via acidic hydrolysis

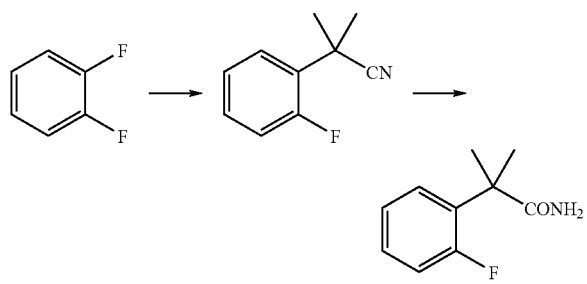

A 500-mL flask equipped with a nitrogen inlet, an addition funnel, magnetic stirring bar, temperature controller, condenser, and a cooling bath was charged with 1,2-difluorobenzene (22.8 g, 0.20 mol), 2-methylpropionitrile (13.8 g, 0.20 mol) and tetrahydrofuran (160 mL). Isopropylmagnesium chloride (2M in THF, 100 mL 0.20 mol) was added from the addition funnel within 30 minutes. The solution was heated to 65° C. for 6 hours. Upon cooling in an ice bath, 6N HCl (100 mL) was added dropwise so the temperature did not exceed 30° C. The mixture was transferred into a separatory funnel and the phases were separated. The aqueous phase was extracted with ethyl acetate. The combined organic extracts were washed with 20% brine and dried with anhydrous sodium sulfate. Filtration and evaporation yielded a light-orange liquid (12.0 g) that was mixed with concentrated sulfuric acid (2 mL) and water (1.25 mL) and the mixture was heated at 65° C. for 8 hours. Water (25 mL) was added causing precipitation of an off-white solid. After cooling to ambient temperature and slurring the solids in water, the suspension was filtered and the solids washed with water. Drying under vacuum, followed by drying in a dry box, gave 2-(2-fluorophenyl)isobutyramide (8.6 g).

Example 15

Scaled-Up Preparation of 2-(2,3-difluorophenyl)-2-methylpropionitrile and 2-(2,6-difluorophenyl)-2-methylpropionitrile

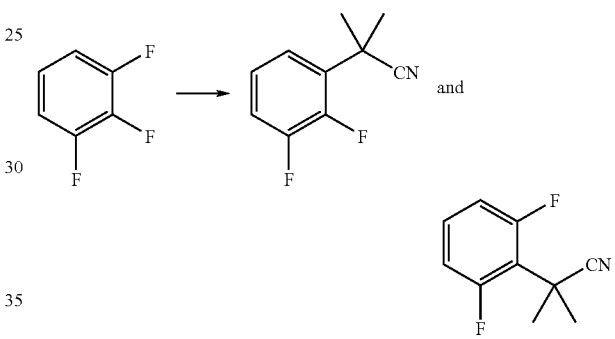

A 1-L, four-necked flask equipped with a nitrogen inlet, an addition funnel, an overhead mechanical stirrer, temperature controller, condenser, and a cooling bath was charged with 1,2,3-trifluorobenzene (33.7 g, 0.255 mol), 2-methylpropionitrile (17.6 g, 0.255 mol) and tetrahydrofuran (200 mL). The solution was cooled with ice/water. Isopropylmagnesium chloride (2M in THF, 128 mL, 0.256 mol) was added from the addition funnel maintaining the temperature between 4.1 and 5.1° C. After 50 minutes, the cooling bath was replaced with a heating mantle and the reaction mixture was gradually heated to 65° C. and stirred at this temperature for 3 hours. The solution was cooled in an ice bath and 5% HCl (150 mL) was added dropwise from the addition funnel. The two liquid phases were separated and the aqueous phase was extracted with THF. The combined organic extracts were washed with brine (3×50 mL) and dried over anhydrous sodium sulfate. Filtration and evaporation of the filtrate gave an oil (28.3 g) that was distilled under reduced pressure (85-97° C./3.3-3.5 torr) to give 21.9 g of a 79/21 (by GC/MS; RT 7.23 and 7.80 min., respectively) mixture of 2-(2,3-difluorophenyl)-2-methylpropionitrile and 2-(2,6-difluorophenyl)-2-methylpropionitrile, respectively. $^1$H-NMR (DMSO-d$_6$): δ 7.55-7.46 (m), 7.33-7.28 (m), 7.21-7.18 (m), 1.83 (m, minor CH$_3$), 1.76 (s, major CH$_3$) (16:84, respectively). A sample of this mixture of isomers was subjected to chromatography on silica gel with 0-4% ether in hexane to give 2-(2,3-difluorophenyl)-2-methylpropionitrile [$^1$H-NMR (DMSO-d$_6$): δ 7.52-7.46 (m, 1H), 7.33-7.29 (m, 2H), 1.76 (s, 3H)] and 2-(2,6-difluorophenyl)-

2-methylpropionitrile [¹H-NMR (DMSO-d₆): δ 7.55-7.46 (m, 1H), 7.21-7.18 (m, 2H), 1.84-1.82 (m, 3H)].

Example 16

Hydrolysis of 2-(2,3-difluorophenyl)-2-methylpropionitrile

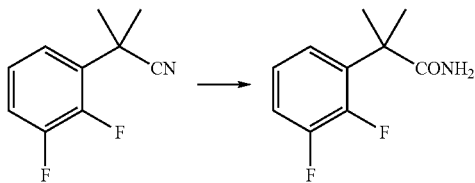

Hydrolysis of 2-(2,3-difluorophenyl)-2-methylpropionitrile was performed according to the procedure of Example 10 using sodium hydroxide in the presence of hydrogen peroxide to provide 2-(2,3-difluorophenyl)isobutyramide [¹H-NMR (CDCl₃): δ 7.17-7.08 (m, 3H), 5.98 (br s, 1H), 5.45 (br s, 1H), 1.60 (s, 6H)].

Example 17

Hydrolysis of 2-(2,6-difluorophenyl)-2-methylpropionitrile

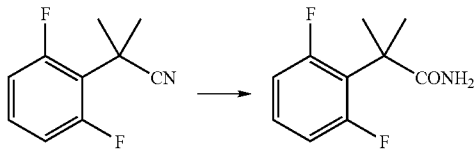

Hydrolysis of 2-(2,6-difluorophenyl)-2-methylpropionitrile was performed according to the procedure of Example 10 using sodium hydroxide in the presence of hydrogen peroxide to provide 2-(2,6-difluorophenyl)isobutyramide [¹H-NMR (CDCl₃): δ 7.34-7.29 (m, 1H), 6.91-6.85 (m, 2H), 6.43 (br s, 1H), 5.73 (br s, 1H), 1.68-1.66 (m, 6H)].

Example 18

Cyclization of 1-(2,6-difluorophenyl)cyclopropanecarboxylic acid amide to 4'-fluorospiro[cyclopropane-1,3'-indol]-2'(1'H)-one

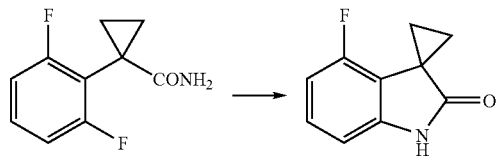

Lithium hydride powder (0.054 g, 6.75 mmol) was placed in a 25-mL flask equipped with a thermocouple, condenser with nitrogen inlet, septum and a magnetic stirring bar. 1-(2,6-Difluorophenyl)cyclopropanecarboxylic acid amide (0.443 g, 2.2 mmol) was dissolved in N,N-dimethylformamide (DMF—4.5 mL) and the solution was added into the flask via a syringe. The suspension was heated to 120° C. and kept at this temperature for 4 hours. Upon cooling, the reaction mixture was transferred into a separatory funnel, diluted with water (fizzing) and 5% hydrochloric acid solution, and extracted with ethyl acetate (3×). The combined organic extracts were extracted with 20% brine (3×) and dried over anhydrous magnesium sulfate. Filtration and evaporation gave yellowish solid (0.327 g, 82% yield). M.p. 171.1-172.2° C. (from ethyl acetate). GC/MS: m/z 177 (purity 98.6%, RT 10.30 min.). ¹H-NMR (DMSO-d₆): δ 10.8 (br s, 1H), 7.22-7.15 (m, 1H), 6.79-6.71 (m, 2H), 1.78-1.74 (m, 2H), 1.47-1.42 (m, 2H).

Example 19

Cyclization of 2-(2,3-difluorophenyl)isobutyramide to 7-fluoro-3,3-dimethyl-1,3-dihydroindol-2-one

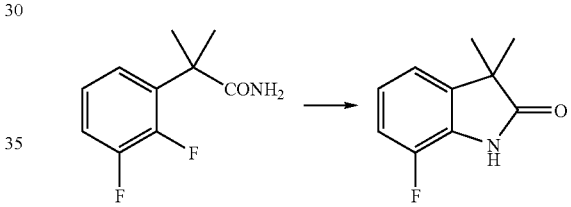

2-(2,3-Difluorophenyl)isobutyramide was cyclized to 7-fluoro-3,3-dimethyl-1,3-dihydroindol-2-one using the LiH/DMF conditions set forth in Example 18 [¹H-NMR (DMSO-d₆): δ 10.85 (br s, 1H), 7.16-6.94 (m, 3H), 1.26 (s, 6H); GC/MS: m/z 179 (100%), RT 8.24 min.].

Example 20

Cyclization of 2-(2,6-difluorophenyl)isobutyramide to 4-fluoro-3,3-dimethyl-1,3-dihydroindol-2-one

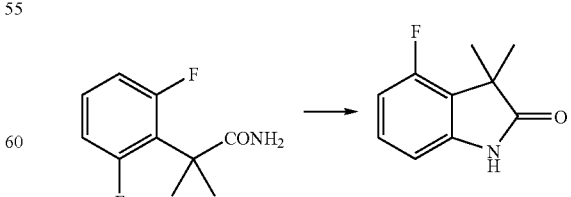

2-(2,6-Difluorophenyl)isobutyramide was cyclized to give 4-fluoro-3,3-dimethyl-1,3-dihydroindol-2-one using the LiH/DMF conditions set forth in Example 18 [¹H-NMR (DMSO-d$_6$): δ 10.60 (br s, 1H), 7.32-7.20 (m, 1H), 6.77-6.70 (m, 2H), 1.34 (s, 6H); GC/MS: m/z 179 (164, 100%), RT 8.99 min.].

Example 21

Cyclization of 1-(2,6-difluorophenyl)cyclopropanecarboxylic acid amide Using Various Organic Bases as Solvents, at 90 and 120° C.

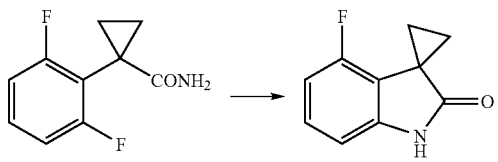

The reaction tubes of Mettler Toledo MiniBlock™ were independently charged with 1-(2,6-difluorophenyl)cyclopropanecarboxylic acid amide (0.1 g) and the following organic bases were independently added (1 mL each): diisopropylethyl amine (Hünig's base), 2,6-lutidine, N-methylmorpholine (NMM), 2,6-di-tert-butyl-4-methylpyridine (1 g, low melting solid, mp 33-36° C.), 1,8-diazabicyclo[5.4.0]undec-7-ene (DBU), and 1,1,3,3-tetramethylguanidine (TMG). The vessels were heated at 90° C. for 3 hours and upon cooling, analytical samples were withdrawn and subjected to GC/MS. The chromatograms revealed only the substrate and no product formed. The vessels were re-heated to 120° C. and kept for 6 hours. Again, GC/MS showed no product formed.

These data indicate that stronger bases than the listed above are necessary for the cyclization to occur.

Example 22

Cyclization of 2-(2-fluorophenyl)isobutyramide Under Various Conditions (Base, Solvent, Temperature)

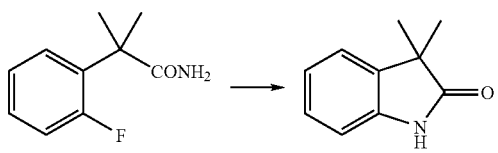

The reaction tubes of Mettler Toledo MiniBlock™ were independently charged with 2-(2-fluorophenyl)isobutyramide (0.1 g), a solvent identified in Table 4 (4 mL each), and two equivalents of a base selected from solid lithium hydride (LiH), solid lithium hexamethyldisilazide (LiHMDS), and 2M lithium diisopropylamide (LDA) in heptane/THF/ethylbenzene. The mixtures were heated to 110° C. and stirred magnetically for 4 hours. Upon cooling to ambient temperature, samples (0.2 mL) were withdrawn, quenched with 5% HCl (1 mL), and extracted with ethyl acetate (1 mL). The organic phases were analyzed by GC/MS: m/z 161 (146, 100%), RT 9.18 min.

TABLE 3

Normalized (area %) of the product distribution

| Base | Solvent | Product |
|---|---|---|
| LiH | N,N-dimethylformamide | 97 |
| LiH | N-methylmorpholine | 0 |
| LiH | toluene | 0 |
| LiHMDS | N,N-dimethylformamide | 76 |
| LiHMDS | N-methylmorpholine | 4 |
| LiHMDS | toluene | 65 |
| LDA | N,N-dimethylacetamide | 15 |
| LDA | 1-methyl-2-pyrrolidinone | 44 |
| LDA | 2-methyl-3-pentanone | 0 |
| LDA | 2,4-dimethyl-3-pentanone | 0 |

In a similar experiment, the bases identified in Table 4 were added in THF and the reaction mixtures heated at 65° C. for 16 hours.

TABLE 4

Normalized (area %) of the product distribution

| Base | Product |
|---|---|
| LiH | 0 |
| LiHMDS | 6 |
| NaHMDS | <1 |
| iPrMgCl | 0 |

These data suggest that the solvent, base, and temperature are important in determining the optimal conditions for the cyclization.

Example 23

Cyclization of Various halo amides and thioamides

The reaction tubes of Mettler Toledo MiniBlock™ were independently charged with the following an amide selected from 2-(3-chloropyridyn-2-yl)isobutyramide, 2-(2-fluorophenyl)-bicyclo[2.2.1]heptane-2-carboxylic acid amide, and a mixture of 2-(2,3-difluorophenyl)isobutyrthioamide and 2-(2,6-difluorophenyl)isobutyrthioamide. N,N-Dimethylformamide (2 mL each) was added to each tube, followed by lithium hydride (2 equiv.) and the vessels were heated to 120° C. for 2.5 hours. Upon cooling, the reaction mixtures were quenched with 5% HCl, brine, and ethyl acetate. The organic phases were separated, dried over anhydrous sodium sulfate and analyzed by GC/MS. The following products were identified, respectively:

(i) 3,3-dimethyl-1,3-dihydropyrrolo[3,2-b]pyridine-2-one (m/z 162, 100%; RT 9.56 min.);

(ii) spiro[bicyclo[2.2.1]heptane-2,3'-[3H]indol]-2'(1'H)-one (m/z 213, 146 (100%); RT 12.52 min.);

(iii) 4-fluoro-3,3-dimethyl-3H-benzo[b]thiophen-2-one and 7-fluoro-3,3-dimethyl-3H-benzo[b]thiophen-2-one (m/z 196, 153 (100%); RT 7.68 and 8.19 min.).

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for preparing oxindole compounds comprising the steps of:
   (a) substituting a fluoroarene of formula I with a secondary nitrile in the presence of sodium hexamethyldisilazide or an isopropyl magnesium halide at about −40 to about 0° C.:

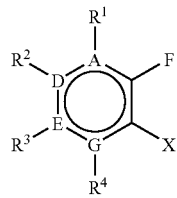

wherein:
   X is halogen;
   $R^1$, $R^2$, and $R^3$ are, independently, selected from the group consisting of H, halogen, CN, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heteroaryl, substituted heteroaryl, $N_2^+$, $OSO_2CF_3$, $CF_3$, $NO_2$, $SR^5$, $OR^5$, $N(R^5)_2$, $COOR^5$, $CON(R^5)_2$, and $SO_2N(R^5)_2$; or
   $R^1$ and $R^2$; $R^2$ and $R^3$; or $R^1$, $R^2$, and $R^3$ are fused to form:
   (i) a 3 to 15 membered saturated or unsaturated carbon-containing ring; or
   (ii) a 3 to 15 membered heterocyclic ring containing in its backbone from 1 to 3 heteroatoms selected from the group consisting of O, S, and $NR^{11}$;
   wherein (i) or (ii) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$;
   $R^4$ is fluorine;
   $R^5$ is selected from the group consisting of $C_1$ to $C_6$ alkyl and $C_1$ to $C_6$ substituted alkyl;
   G is C;
   A, D, and E are, independently, selected from the group consisting of C and N, wherein if any one of A, D, E, or G are N, the corresponding $R^1$-$R^3$ is optionally absent;
   $R^{11}$ is absent, H, $C_1$ to $C_6$ alkyl, substituted $C_1$ to $C_6$ alkyl, aryl, or substituted aryl;
   or a pharmaceutically acceptable salt thereof;
   (b) converting the nitrile substituent of the product of step (a) to an amide; and
   (c) cyclizing the product of step (b) to said oxindole.

2. The method according to claim 1, wherein said oxindole compound is of the structure:

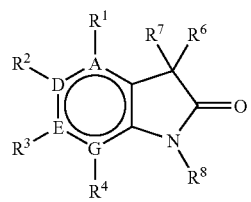

wherein:
   $R^6$ and $R^7$ are independently selected from the group consisting of $C_1$ to $C_6$ alkyl, substituted $C_1$ to $C_6$ alkyl, $C_3$ to $C_{14}$ cycloalkyl, substituted $C_3$ to $C_{14}$ cycloalkyl, aryl, substituted aryl, heteroaryl, substituted heteroaryl, $C_2$ to $C_6$ alkenyl, substituted $C_2$ to $C_6$ alkenyl, $C_2$ to $C_6$ alkynyl, substituted $C_2$ to $C_6$ alkynyl, $N(R^5)_2$, $SR^5$, and $OR^5$; or
   $R^6$ and $R^7$ are fused to form:
   (iii) a 3 to 8 membered saturated or unsaturated carbon-containing ring; or
   (iv) a 3 to 8 membered heterocyclic ring containing in its backbone from 1 to 3 heteroatoms selected from the group consisting of O, S, and $NR^{11}$;
   $R^8$ is selected from the group consisting of H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $CF_3$, aryl, substituted aryl, heteroaryl, and substituted heteroaryl;
   wherein any of (iii)-(iv) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$;
   or a pharmaceutically acceptable salt thereof.

3. The method according to claim 1, wherein said secondary nitrile is $R^6R^7CHCN$, wherein:
   $R^6$ and $R^7$ are, independently, selected from the group consisting of $C_1$ to $C_6$ alkyl, substituted $C_1$ to $C_6$ alkyl, $C_3$ to $C_{14}$ cycloalkyl, substituted $C_3$ to $C_{14}$ cycloalkyl, aryl, substituted aryl, heteroaryl, substituted heteroaryl, $C_2$ to $C_6$ alkenyl, substituted $C_2$ to $C_6$ alkenyl, $C_2$ to $C_6$ alkynyl, substituted $C_2$ to $C_6$ alkynyl, $N(R^5)_2$, $SR^5$, and $OR^5$; or
   $R^6$ and $R^7$ are fused to form:
   (iii) a 3 to 8 membered saturated or unsaturated carbon-containing ring; or
   (iv) a 3 to 8 membered heterocyclic ring containing in its backbone from 1 to 3 heteroatoms selected from the group consisting of O, S, and $NR^{11}$;
   wherein (iii) or (iv) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$.

4. The method according to claim 1, wherein the product of step (a) is:

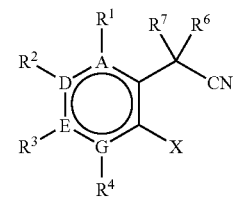

wherein:
   $R^6$ and $R^7$ are independently selected from the group consisting of $C_1$ to $C_6$ alkyl, substituted $C_1$ to $C_6$ alkyl, $C_3$ to $C_{14}$ cycloalkyl, substituted $C_3$ to $C_{14}$ cycloalkyl, aryl, substituted aryl, heteroaryl, substituted heteroaryl, $C_2$ to $C_6$ alkenyl, substituted $C_2$ to $C_6$ alkenyl, $C_2$ to $C_6$ alkynyl, substituted $C_2$ to $C_6$ alkynyl, $N(R^5)_2$, $SR^5$, and $OR^5$; or
   $R^6$ and $R^7$ are fused to form:
   (iii) a 3 to 8 membered saturated or unsaturated carbon-containing ring; or
   (iv) a 3 to 8 membered heterocyclic ring containing in its backbone from 1 to 3 heteroatoms selected from the group consisting of O, S, and $NR^{11}$;
   wherein (iii) or (iv) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$.

5. The method according to claim 1, wherein the product of step (b) is:

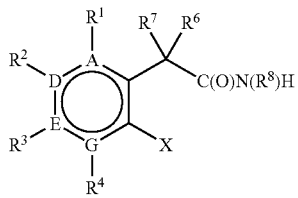

wherein:
- $R^6$ and $R^7$ are independently selected from the group consisting of $C_1$ to $C_6$ alkyl, substituted $C_1$ to $C_6$ alkyl, $C_3$ to $C_{14}$ cycloalkyl, substituted $C_3$ to $C_{14}$ cycloalkyl, aryl, substituted aryl, heteroaryl, substituted heteroaryl, $C_2$ to $C_6$ alkenyl, substituted $C_2$ to $C_6$ alkenyl, $C_2$ to $C_6$ alkynyl, substituted $C_2$ to $C_6$ alkynyl, $N(R^5)_2$, $SR^5$, and $OR^5$; or
- $R^6$ and $R^7$ are fused to form:
  - (iii) a 3 to 8 membered saturated or unsaturated carbon-containing ring; or
  - (iv) a 3 to 8 membered heterocyclic ring containing in its backbone from 1 to 3 heteroatoms selected from the group consisting of O, S, and $NR^{11}$;
- wherein (iii) or (iv) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$.
- $R^8$ is selected from the group consisting of H, $C_1$ to $C_6$ alkyl, substituted $C_1$ to $C_6$ alkyl, $C_1$ to $C_6$ alkoxy, substituted $C_1$ to $C_6$ alkoxy, $C_1$ to $C_6$ aminoalkyl, substituted $C_1$ to $C_6$ aminoalkyl, $C_1$ to $C_6$ thioalkyl, substituted $C_1$ to $C_6$ thioalkyl, $CF_3$, aryl, substituted aryl, heteroaryl, and substituted heteroaryl;
- wherein any of (iii)-(iv) are optionally substituted by $C_1$ to $C_6$ alkyl, substituted $C_1$ to $C_6$ alkyl, halogen, $C_1$ to $C_6$ alkoxy, substituted $C_1$ to $C_6$ alkoxy, or $N(R^5)_2$.

6. The method according to claim 1, wherein step (b) is performed using hydrogen peroxide.

7. The method according to claim 1, wherein step (c) is performed in the presence of a strong base.

8. The method according to claim 1, wherein said fluoroarene is:

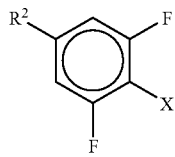

wherein:
X is F, Cl, or Br; and
$R^2$ is Br, Cl, I, or H.

9. The method according to claim 8, wherein said fluoroarene is:

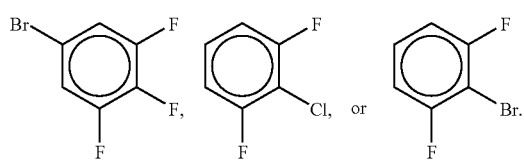

10. The method according to claim 1, wherein the product of step (a) is:

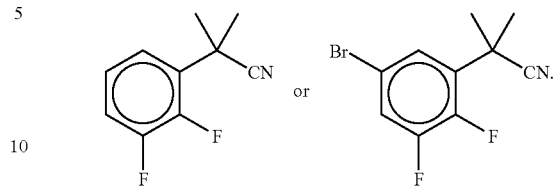

11. The method according to claim 1, wherein the product of step (b) is:

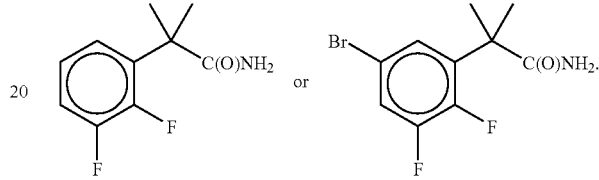

12. The method according to claim 1, wherein said oxindole is of the structure:

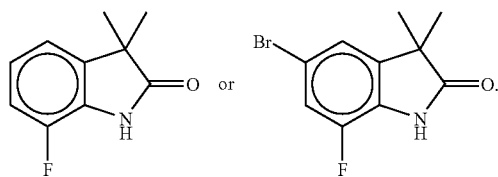

13. A method for preparing 7-fluoro-3,3-dimethyl-indol-2-one, comprising:

(a) reacting 1,2,3-trifluorobenzene with isobutyronitrile in the presence of sodium hexamethyldisilazide or an isopropyl magnesium halide at about −40 to about 0° C. to form a compound of the structure:

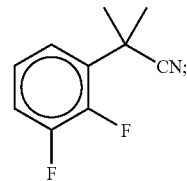

(b) converting the product of step (a) to an amide of the structure:

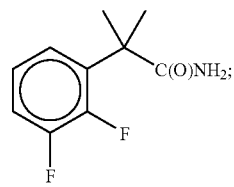

(c) cyclizing the product of step (b) to said 7-fluoro-3,3-dimethyl-indol-2-one.

* * * * *

UNITED STATES PATENT AND TRADEMARK OFFICE
CERTIFICATE OF CORRECTION

PATENT NO. : 7,595,338 B2  Page 1 of 1
APPLICATION NO. : 11/413159
DATED : September 29, 2009
INVENTOR(S) : Bogdan Kazimierz Wilk It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 440 days.

should read (*) Notice: Subject to any disclaimer, the term of this patent is extended or adjusted under 35 U.S.C. 154(b) by 595 days.

Signed and Sealed this

Eighteenth Day of May, 2010

David J. Kappos
*Director of the United States Patent and Trademark Office*